(12) United States Patent
Wayne et al.

(10) Patent No.: US 6,815,537 B1
(45) Date of Patent: Nov. 9, 2004

(54) METHOD FOR CONSTRUCTION OF THERMUS-E, COLI SHUTTLE VECTORS AND IDENTIFICATION OF TWO THERMUS PLASMID REPLICATION ORIGINS

(75) Inventors: Jay Wayne, Flushing, NY (US); Shuang-yong Xu, Lexington, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/664,186

(22) Filed: Sep. 18, 2000

Related U.S. Application Data

(63) Continuation of application No. 09/134,246, filed on Aug. 14, 1998, now Pat. No. 6,207,377.

(51) Int. Cl.[7] .................. C07H 21/04; C12N 15/74
(52) U.S. Cl. ................. 536/23.1; 536/24.1; 435/320.1
(58) Field of Search ................. 536/23.1, 24.1; 435/320.1

(56) References Cited

PUBLICATIONS

Wayne et al. The Tsp–45I restriction modified system is plasmid–borne within its thermophilic host. Gene vol. 202:83–88, 1997.*
Munster et al, Appl. Environ. Microbiol., 50:1325–1327 (1985).
Kristjansson et al., 'Thermophilic Bacteria', Kristjansson, ed., p. 1–18 (1992).
Hishinuma et al., J. Gen. Microbiol. 104:193–199 (1978).
Eberhard et al., Plasmid 6:1–6(1981).
Vasquez et al., FEBS Lett. 158:339–342 (1983).
Kristjansson, Trends Biotech. 7:349–353 (1989).
Coolbear et al., Adv. Biochem. Eng. Biotech. 45:57–98 (1992).
Wiegel et al., CRC Crit. Rev. Biotech. 3:39–108 (1984).
Koyama et al., J. Bacteriol. 166:338–340 (1986).
Raven et al., Nucl. Acids Res. 21:4397 (1993).
Oshima et al., J. Sys. Bacteriol. 24:102–112 (1974).
Wayne et al., Gene 195:321–328 (1997).
Sambrook et al, 'Molecular Cloning A Laboratory Manual', 2nd ed. (1989).
Hartmann et al., J. Bacteriol., 171:2933–2941 (1989).
Maseda et al., FEMS Microbiol. Lett. 128:127–134 (1985).
McMacken et al., DNA Replication (Chapter 39) p 586–587 in *Escherichia coli* and Salmonella typhimmarium, Amer. Soc. for Microbiol., Washington DC.
de Grado et al., FEMS Microbiol. Lett., 165(1):51–57 (1998).

* cited by examiner

*Primary Examiner*—Terry McKelvey
*Assistant Examiner*—Nancy T. Vogel
(74) *Attorney, Agent, or Firm*—Harriet M. Strimpel; Gregory D. Williams

(57) ABSTRACT

The present invention relates to cloned DNA containing origin of DNA replication and to cloned DNA encoding repliation protein, RepT.

3 Claims, 13 Drawing Sheets

FIG. 1

```
         10                  30                  50
GTGAAGAACGAAAAAACCTTCTTTGAAGAGCTTTACGAGGCTTTAGAGGAAACCCACGAC
         M  K  N  E  K  T  F  F  E  E  L  Y  E  A  L  E  E  T  H  D
         70                  90                 110
AACACCGATGCCACTAGGGGGTCAGATAGGGGGTCAGAGGACTTCTTCTTGGCCACCGAC
 N  T  D  A  T  R  G  S  D  R  G  S  E  D  F  F  L  A  T  D
        130                 150                 170
CCCCCTCCAGATGGAGGTGCCGAAAATCGCCTCGCGAAGGGCTTTACATACCAAAAAGAG
 P  P  P  D  G  G  A  E  N  R  L  A  K  G  F  T  Y  Q  K  E
        190                 210                 230
GCACTTAGGATTGCTTTACCCGAGAAAGACCATGAGGCTTTCCTTTCCTCTGTTGGGGCC
 A  L  R  I  A  L  P  E  K  D  H  E  A  F  L  S  S  V  G  A
        250                 270                 290
CCCCCTATACCACCAGCTGAACCCCCCGTTGGGAATGTATGTCAAGCCGTCCAGGACGGG
 P  P  I  P  P  A  E  P  P  V  G  N  V  C  Q  A  V  Q  D  G
        310                 330                 350
CCTCAGAAGCTTCTGGAACTCCTCCAGGAGATTGCCCGCTCCACCATCCCCTACGGCAAC
 P  Q  K  L  L  E  L  L  Q  E  I  A  R  S  T  I  P  Y  G  N
        370                 390                 410
CGGGAGCTCTGGAGGAAGGTGGGGACGGTCGTCTTCATGGTCCCCCTGGAGATGTTGGCC
 R  E  L  W  R  K  V  G  T  V  V  F  M  V  P  L  E  M  L  A
        430                 450                 470
CTCAACCTGGGGGTCACCCGGCAGACCGTCCACGCCTGGAAGAAGGTCCTTGAGAAAAAG
 L  N  L  G  V  T  R  Q  T  V  H  A  W  K  K  V  L  E  K  K
        490                 510                 530
GGCCTGGTGGCCACCGACGTCCTTCACCAAACCGTCAACGGGGAGCGCCGGGCCATCGGC
 G  L  V  A  T  D  V  L  H  Q  T  V  N  G  E  R  R  A  I  G
        550                 570                 590
ACCCTTTGGGCCGTCCGGCTGAGGCCAGGGAAAGCCAGGCTCACCCTGGACGACTACATC
 T  L  W  A  V  R  L  R  P  G  K  A  R  L  T  L  D  D  Y  I
        610                 630                 650
TACCCCTGGAGGAACCTCGCCCTAGACATGGCCAACGGCGTGCTCTCCTTCAACTGGGTC
 Y  P  W  R  N  L  A  L  D  M  A  N  G  V  L  S  F  N  W  V
        670                 690                 710
AAGGCCTACCAGGACCACGGAATCCGCCCCACCCTGGACGTGCTGGTCCTCTGGGCTCAG
 K  A  Y  Q  D  H  G  I  R  P  T  L  D  V  L  V  L  W  A  Q
        730                 750                 770
GGGAAAAGGGTGATGCCCAACACCAAGACCGTGGCCGTTGACCTGGGCCTCATCCTGGTC
 G  K  R  V  M  P  N  T  K  T  V  A  V  D  L  G  L  I  L  V
        790                 810                 830
CTCCCCGAGGTGGAGCGTTCCAAACTCCCGGCCCTTATCACCCTCATTGCTACGTACATT
 L  P  E  V  E  R  S  K  L  P  A  L  I  T  L  I  A  T  Y  I
        850                 870                 890
GCCGATCTCCTAGATGACCGTCGTTCAAGACGTTTCTATGCAGGCTTGCTGTGGGCTGTG
 A  D  L  L  D  D  R  R  S  R  R  F  Y  A  G  L  L  W  A  V
        910                 930                 950
GCCAGGGGTGAACTCCCCGCGCAATATCTATTTGCCGTCCTAATGCGGGTTATCCGAGAT
 A  R  G  E  L  P  A  Q  Y  L  F  A  V  L  M  R  V  I  R  D
        970                 990                1010
TACACGGATGGCCATCTGACACGACCGGGAGCGTACCTAGTGAAGACCCTCAAGGAGGCC
 Y  T  D  G  H  L  T  R  P  G  A  Y  L  V  K  T  L  K  E  A

TCCTGA
 S  *
```

FIG. 2

```
          *              *              *              *              *
  1  CTATAACGGCCTTTTAGGAGGGGGGATTGCCAGCCGCTGGGCTGACGGTTATTTTGGACC

61  CATAAAAAGGCGAAACCGAGGCGGTTGCCCCGGATCACCCCCAAGACCTAGGGTAACGCC

121  TCGGGCTCCAGATGACAAGGAGGTCCGAGGGTGAAGAACGAAAAAACCTTCTTTGAAGAG
                                     M  K  N  E  K  T  F  F...(RepT)
```

FIG. 3A

```
   1 tctagaaggt cagggtggac aaggaaaaca ccatagcccc tgccaagaag atggacgagt
  61 tggtgtccgg aaaagtggcc atccggggcg ctcttgacaa ctatttttcca gcggtggcca
 121 ccggcattgg ccacgaggta cgagcttgtg gagtagacgg ccacaaaggg gtcgtcctca
 181 aacttctttt ctagtgccgc ttggacgaag gggaggaaga ggaaaggctt catggcctca
 241 cctccttccc ctcctccttg gcggccttag cggcgtaaaa ctctgagacg gcctgaagtt
 301 tagggatttc gctttcgggg ataagaatcc ggcggctcag gggatgccgg atgccctta
 361 tcctgccgtc ccttatgtac tcgtaaatgg tggccttggg tactttaaac cgttctgaaa
 421 cttctctaac agagagcaca aaacctctaa aaacctatca atcccaccga ttccagtata
 481 ccataaatgg cacaaagttt tgagaaggtg gtcaaacaaa aaggctttct cggtcaggtt
 541 atggtgaggt ggggcggtc aaaggccgac ttaagtttgg taaagccggg aggaagcaaa
 601 ccggggtgtt accatgcaac agatggccga gtggaacgtg tggacacaga gaagcgttga
 661 gcttctggag aaggggtatt tggataaact actgcaggtc tataaagggg aaagtggctc
 721 ttcgaggtca gtaccagagg aggtagagga aaaacttcgc gaggcctaca aggcatacga
 781 ggggaggcag gatagtccgg aggcagaaac gaaactcgtg gaagccgtgc taaatgccag
 841 aaaaaaggtc gagcggtccc ccttcaatca ccccctacctg cctttggtct actacctggt
 901 ttcggaaaaa gcagaaaaag cgaacaaggc ccttgaggag gcattgcagg aggttgcctc
 961 aaagcaccca gaaaccatcc gcgtcctggc caaggaagcg caaagaagag gcgtagaagc
1021 cttgatccaa aggctcaagg agcctcccga aataaatcgg cagatagggc cgatgttcaa
1081 aaggtggtac aaagaagagc taaaggggaa aatagaagag aggcttccag gccctaccaa
1141 accaaagatt gtggtagtat cccctgaaaa aagtaaaccg gagcaagcac cccttattgc
1201 ggagagagaa gcgggcatca tcatatacac gggatcggat gaagctttga aagatgccgc
1261 caaggaaaac ctgggccttg gcgaggaagc agaactaggc accaagggcg tagatttcta
1321 cgtggtcatc cggcgtagcc ctgaagagac atggcaccta acaggagaag tgaagtttca
1381 atccgacttt ggcggaaacc aagacaacca gaaactagta gcaaaggctt ccataaggtt
1441 ggaccttgag aagaggcaca taggaatagt ggtggtggac ggaatgcctg tggtgagcaa
1501 gtttcgtggg tggccggac tggggaaaga aacgatcgtt acatccgtac tcctccttcc
1561 agacctgata gcggagctct accaaaaggg tgaagaagcc ctgggcctct agaaggcgga
1621 cacaatctca aacttgtgct gtagcctggg gaaatcctct aacacccttc tagtgaaggc
1681 tttgaccgcc tcccaggagg catctatgcc gatggatcgc cgctttaaga ggggtgaggc
1741 tataagcgta gtaccggagc ctgcgaaggg atcgagcact aaatccccct cgttactccc
1801 tgtttggacg atgagcttga gcatgtccag atttttctcg gtggggtatc gcgggtacgg
1861 aggatccttg aactgccaaa cgtcctggag cttcttcccc ttcttcaggc gatcccgagc
1921 gtaaactttc ttccgcggca ccccgttctt tgaccagaca ataagccctt gagcgtctag
1981 ctcgtcaagc ttctccgggg gatagcgcca atgccgtcca ggaggggggaa gtattcctcg
2041 ccaaggcctt ccggtagggc catccttggt ttctccagga gcatgcaggg gattggtggt
2101 gtaccgttcc ccgttctcgt ctacaaaggg gaaaagccta gcgatctcct cttccgaata
2161 gggctagcc gattcgttcc aaacgtagtc ccgcgttttg gagtagacga ggatcatgtc
2221 cttttgcgat ccgaaggcct tacgggaaaa gttttttggga tttgaagcga tgcgggcgat
2281 atggttaacg aagtttcgcc ggccaaagac ctcatcaagg atgagcttca cctcgaaccc
2341 gtatttctcg tctatgtgaa cgaagatcag tcctgagtcc gccatcagct ccctgagaag
2401 tatcaagcgc tccctcagga actccacaaa ctgaggacca tcgagggtgt catcgtagcc
2461 caactgaccg ttttttgggct ggctgacggt agcaacgcga tctgtttcat cgccgccaac
2521 gagaaactgc tggccggttc cataaggcgg gtcaatatag accaactgga ccttccccgc
2581 atacccacca ggctcccgga gcatccaccg gagaacctga ccgttttccc ccaaaaagta
2641 ggtgccaata ggatcaatct caaaaagggg ggcatttccc cctaggaaga ggagggtttc
2701 ttttcgcaaa acaagttgtg gggtgggctg atcaagaatc tccttctcat cgcgttttcc
2761 ggggtagacc aacctaaagg gcgaaggttc cgaggttttc gaggctttca aggggggctt
2821 tcgggtcaaa ccagggtagc tacggctcat tcttccctcc ccacagcgct cttaagcagg
2881 acctcatcac ccacaaccct cacgcactcc aaccaaggaa tccgccaaag gcggcctacc
2941 ttttgagccc gtatcttccc ctgacgtata gaccttcgga tcgtctcagg gtgcacccga
3001 aggatgtctg caagctcctc gggggtcagg tacacgggct tcatcctcat gacacaacct
3061 tacccacag aggacaacac atgcaactat gggcaaagta gacaacgaga ccaaaagctt
3121 gggccactct ctcaggaggc ctccttgagg gtcttcacta ggtacgctcc cggtcgtgtc
3181 agatggccat ccgtgtaatc tcggataacc cgcattagga cggcaaatag atattgcgcg
3241 gggagttcac ccctggccac agcccacagc aagcctgcat agaaacgtct tgaacgacgg
3301 tcatctagga gatcggcaat gtacgtagca atgagggtga taagggccgg gagtttggaa
```

FIG. 3B

```
3361 cgctccacct cggggaggac caggatgagg cccaggtcaa cggccacggt cttggtgttg
3421 ggcatcaccc ttttcccctg agcccagagg accagcacgt ccagggtggg gcggattccg
3481 tggtcctggt aggccttgac ccagttgaag gagagcacgc cgttggccat gtctagggcg
3541 aggttcctcc aggggtagat gtagtcgtcc agggtgagcc tggctttccc tggcctcagc
3601 cggacggccc aaagggtgcc gatgcccgg cgctcccgt tgacggtttg gtgaaggacg
3661 tcggtggcca ccaggcctt tttctcaagg accttcttcc aggcgtggac ggtctgccgg
3721 gtgaccccca ggttgagggc caacatctcc aggggacca tgaagacgac cgtccccacc
3781 ttcctccaga gctcccggtt gccgtagggg atggtggagc gggcaatctc ctggaggagt
3841 tccagaagct tctgaggccc gtcctggacg gcttgacata cattcccaac gggggttca
3901 gctggtggta taggggggc cccaacagag gaaaggaaag cctcatggtc ttctcgggt
3961 aaagcaatcc taagtgcctc ttttggtat gtaaagccct tcgcgaggcg attttcggca
4021 cctccatctg gaggggtc ggtggccaag aagaagtcct ctgaccccct atctgacccc
4081 ctagtggcat cggtgttgtc gtgggtttcc tctaaagcct cgtaaagctc ttcaaagaag
4141 gttttttcgt tcttcaccct cggacctcct tgtcatctgg agcccgaggc gttaccctag
4201 gtcttggggg tgatccgggg caaccgcctc ggtttcgcct ttttatgggt ccaaaataac
4261 cgtcagccca gcggctggca atccccctc ctaaaaggcc gttataggcc ctgctaggag
4321 gggggtagta cttcctacc cccctaggct tggagaggcc ttaggaggtc tcctagggcc
4381 tcgtgggggt gtaggggtaa cctcatggcc aggccggccg gctcgggact ctggaggagg
4441 cctccatagc ctactcgtgg tggaggtttg tgaagggt cactaatgca tacggctagc
4501 ctcgggatca cggccaaatg gtatgcaggt tttggtataa aaccctcagg tttgaggcta
4561 gtttatgtcg gttttatgca cctttgactc ggatcacggg cataaacacc agtttcctgc
4621 acgaaagaaa actttcgcga tctaagaggg ggaaagaggt gtagagggac ggccttcatg
4681 aaagttggcc tcttaggagg ccgttgtaga gggccgtctc gggttcaaat ccttccctc
4741 tctctccagg tttccgaggt tcgaggtctt ggtccaggtc ttgtaccaag ttttgacca
4801 aagtctattc tcggaatata ggggtatctt gtctatcttc cctacgggat atctctgtct
4861 gtgtgaactt gatcccatcc caatacatat ctcaatctcc taatctcctc ttctctccag
4921 atccctaatc tcttcttcta cctctttctc ctcccaatta agaatggaga ggaaaaaccc
4981 cgaccagaac gagcttctcg gggtcagttt cggtaatctc gggacaggtt ttcatcgtct
5041 aggacgagga ttagggcatg aaaaatgggc tttgacaaaa tctttctaaa aaatactccc
5101 cgaggttggg gaagtgccct cggggagaag attttggca gtttagatgt tatgctctat
5161 cacgggccgg aggcctccac gataagttgt cttggccaag taccgggcca ggtcggggt
5221 gctcttcagc gtggtgatgg tactttcacg gaagttcaca agtccttta gaggcttcag
5281 gtcggggata gtgctcaagt actcccaagc gttctcgggc ccgtggtcgg ggagaaggac
5341 aaaggggtcg ggcaaaagtt catctttgta cttaggacgg attactttag cacctgataa
5401 cttcagggcc gttaagaagg gcctcacctc ggagacgggt ggaaggagga cgtgggcgtg
5461 gaagaagacg aaccccgatt tttgggaagt ctccctccag tttgatgatg aacgttggga
5521 ggaagccggc caggatgtct ttcatcgcgc ctcgaacctc ggacacataa aaaactttcg
5581 tgtttgtcag ggcaagagtg ctatgtatga ggtaaccttc gggagtacaa agtgcctcaa
5641 gccgcctttc ccaacgctcc aaaactctag ggtcaggtgg tttaggtttt ctgaaaaact
5701 ctagcttttc agtggtcatt cctcaccct ctagcacgta ctctggaagg taaacctttg
5761 acacagcggc caagtctagc gtctcccagt ccagttggtc tgggacgcgt gagaagggga
5821 ggggcttggt gtagaggacc agaagaccc
```

FIG. 4

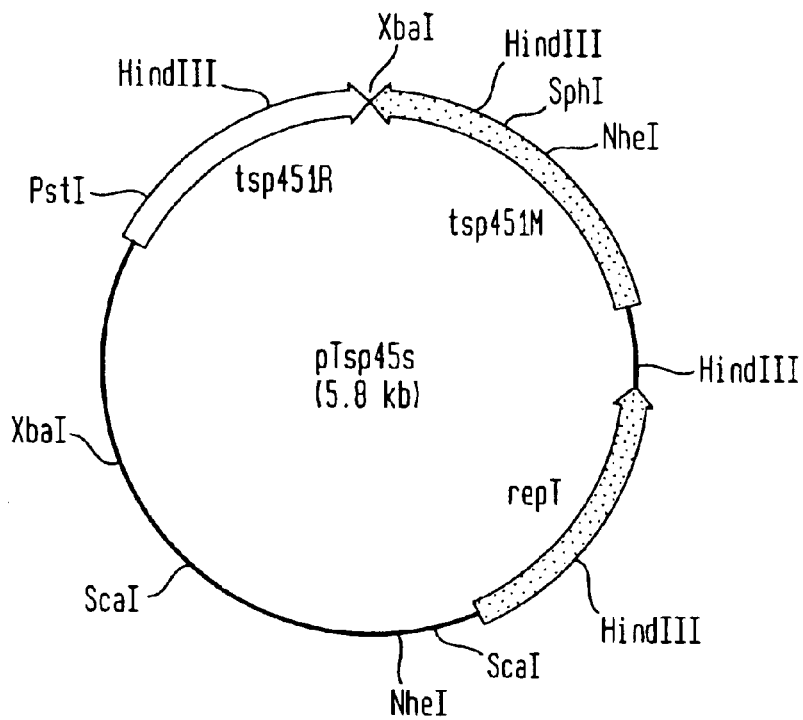

FIG. 5

```
  1 ATGATCGTGGCTGTCACCGGCTTCAAGGGAGGGGTGGGGAAGACCACCACGGCGGTCCAC
    M  I  V  A  V  T  G  F  K  G  G  V  G  K  T  T  T  A  V  H
 61 CTGGCCTGCTTCCTGGCCGAGCGGGGCCCCACCCTGCTGGTGGACGGGGACCCCAACCGC
    L  A  C  F  L  A  E  R  G  P  T  L  L  V  D  G  D  P  N  R
121 TCCGCCACGGGGTGGCACCGGAGGGGAGGCCTCCCGGTGACCGTGGTGGACGAGCGGGTG
    S  A  T  G  W  H  R  R  G  G  L  P  V  T  V  V  D  E  R  V
181 GCGGCCCGGTACGCCCGGGAGCACGCCCACGTGGTCATAGACACCCAGGCCCGCCCCACG
    A  A  R  Y  A  R  E  H  A  H  V  V  I  D  T  Q  A  R  P  T
241 GAAGAGGACCTCCGGGCCCTCGCCAAGGGGGTGGACCTGCTGGTCCTGCCCACGTCCCCC
    E  E  D  L  R  A  L  A  K  G  V  D  L  L  V  L  P  T  S  P
301 GACGCCCTGGCCCTGGAGGCCCTCCTGGCCACCCTGGAAGCCCTGCGGGGGGCGGAGGCC
    D  A  L  A  L  E  A  L  L  A  T  L  E  A  L  R  G  A  E  A
361 CGCTTCCGGGTCCTCCTGACCATGGTGCCCCCGCCCCCGAGCCGGGACGGGGAGGAGGCC
    R  F  R  V  L  L  T  M  V  P  P  P  P  S  R  D  G  E  E  A
421 CGGGCCCTCTTGGGGGCGGAGGGCGTTCCCCTCTTCACAGGCTGGGTGAGGCGGGCGGCA
    R  A  L  L  G  A  E  G  V  P  L  F  T  G  W  V  R  R  A  A
481 GCCTTCCCCAAGGCCGCCCTCCTGGGGGTGCCTGTCTACCGGGTGCCCGACCCCAGGGCG
    A  F  P  K  A  A  L  L  G  V  P  V  Y  R  V  P  D  P  R  A
541 AGGCTGGCCTGGGGGGACTACGCGCGGGTGGGGGAAGAGCTCCTGAAGGAGGTGGGGGGA
    R  L  A  W  G  D  Y  A  R  V  G  E  E  L  L  K  E  V  G  G
601 TGA 603
```

FIG. 7A

```
      CTTATACACACAAACTATACACGTCTCTATCGGGCTTTTCTTAGCGCCATGTAAAACACC
  1   ------------+----------+----------+----------+----------+----------+   60
      CCTCCCATCTCCGGGTGTTTACAGCGGATACGGGAGGTTCAGCGGGAACTTTTCCCCTTG
 61   ------------+----------+----------+----------+----------+----------+  120
      TTGAAACTTTGGGGTCTGAGGCTCAACAGCAGAACAGCTTAGGTTGACTCAACACAGCTC
121   ------------+----------+----------+----------+----------+----------+  180
      ATAAGTCCCTTCATTATCGCCTGAGTCAACCTATGAGTTAACCTTTTTTCAAGAAAAAGA
181   ------------+----------+----------+----------+----------+----------+  240
      GATAAGTGAGTTTTGTCCTCTAGCACGACTTTTTTCTTTGAGTCAACCTCTGTGCCGACC
241   ------------+----------+----------+----------+----------+----------+  300
      CCCCCGATTTTGAGTCAACCCCCCTTTGAGCCGAAACTTTGTTGGCACAGGGGTTGACTC
301   ------------+----------+----------+----------+----------+----------+  360
      AGGGGTTGACTCAACGCGAATGGCCTCTGGAAGGGCGTTGAGCCGACCCCTCCCTCGTGT
361   ------------+----------+----------+----------+----------+----------+  420
      GCCGACCCCGCTCCACTATGAGCAGGGGGGAAAGTTACGGGAAAAGTTCCCCAAGTCCC
421   ------------+----------+----------+----------+----------+----------+  480
      CCTTGACAAAAGATGACAATCGAGTTAATGTCACAGCGATGCGTCACTCACCTCTGGCTG
481   ------------+----------+----------+----------+----------+----------+  540
      GGCTCACCCAGATGCGTGCGCGAACGTTTCAGAGCCTCCTTCGATTCCTGGCCAGGGAGG
541   ------------+----------+----------+----------+----------+----------+  600
      GGCGCTACCCCACTGGTGTAGAGCTCGCCAAGGTGCTGGGGCGCAGCCCGCACGCCACGT
601   ------------+----------+----------+----------+----------+----------+  660
      GGGCCATGCTCAGGGCTTTGACCCGTCATGGACTCGTGGAACGGCACGAGGGGGTCTATG
661   ------------+----------+----------+----------+----------+----------+  720
      TTCTGACCCCTGCGGGCGTAGAACTTGCCAGGACCCTGGGAACCACCGTGTGGCGTGGGG
721   ------------+----------+----------+----------+----------+----------+  780
      ATGAGGAGGTACAGACGGCGTTACAGCTGCTAGGAGTCGGTCATGCCGCCGAGGACAGGC
781   ------------+----------+----------+----------+----------+----------+  840
      GCTGAAGCTTTTGAGCCGGGGCCCTCACCCAAGGCCACCCCGGCTCCTCTCCCCTGGGAT
841   ------------+----------+----------+----------+----------+----------+  900
      CCCAAATGGATCCCTCAGCGCCATTATCCTCCTGGCGGTCCTATAGCGCAAGGAGGTAGT
901   ------------+----------+----------+----------+----------+----------+  960
      GGTGACGAAACACACAAATGTTTCACCCCACCTTTTGGATGCCGTAGAGGAGCTCGCTCG
961   ------------+----------+----------+----------+----------+----------+ 1020
      CCAGATTGCTGAAACCGCTAACAAGGCTTATTCCAGCCATTTCAGGCAGATTGTCAAAGT
1021  ------------+----------+----------+----------+----------+----------+ 1080
      CCTGCCGCCTGAGGTTCCCGACCTCTACGCCTGGCTGGCCGCCCTGGATGACTCCGCCAT
1081  ------------+----------+----------+----------+----------+----------+ 1140
      CGAGGAGCTTGCCCAGCGCCTGAGGGAGGTCGAGGGAAGCCCCCGCCCCATTTCACCGC
1141  ------------+----------+----------+----------+----------+----------+ 1200
      CGCCCTCAAAAAGGCCCTGGCCATCGCCCTACAGCGGCGGACCCTCGCCGAGATGCCCC
1201  ------------+----------+----------+----------+----------+----------+ 1260
      CACGTTCGCCAACGCGCTCCGCTGGGCGATGGAACGGCAAGGGGTGAGCATCCGCAAGCT
1261  ------------+----------+----------+----------+----------+----------+ 1320
      TGCGAGAGAGGGTAGGGGTCAGCAAAACCACTGTTAAAAAGTGGCGTGGAGGCCGCTTTGT
1321  ------------+----------+----------+----------+----------+----------+ 1380
      CCCTCGTTCACGGACCTACGTGAGGAGGTTGGAGGAGATCCTGGACCTCCCGGAAGGCGC
1381  ------------+----------+----------+----------+----------+----------+ 1440
      CCTTTCGGGACGACTACCCCGCTGGGGGTTGCCAAAAATATTGGAAGGTGTTGAGGGGAA
1441  ------------+----------+----------+----------+----------+----------+ 1500
      AGATGCCCCTTATCCCGGGTTCACGCGGACCTTCCTGCGCGTGGCCGCCCTGGCGCGCTA
1501  ------------+----------+----------+----------+----------+----------+ 1560
      CGGCCGCCCGTGGGATGATCTCTCTCCCGACGAACAGGAGGCCCTTCGGCGCGAGGACGA
1561  ------------+----------+----------+----------+----------+----------+ 1620
      AGACCGGTGGACCCGCCTCTCCAACCGCCAGAAGCGAGTGCGAAAGGCCAGTCAAAAACC
1621  ------------+----------+----------+----------+----------+----------+ 1680
      TTTTCGGCTTTCCTTTGACGAGTGGCCAACTGAGGCTCGCAAAGAATGGGAGGACTACGA
1681  ------------+----------+----------+----------+----------+----------+ 1740
      GCGCTATGCCTCATCGGCACCTGGGAGCATCGCGCGCGTGCAGGCGGCGCTTGCGGGCGC
1741  ------------+----------+----------+----------+----------+----------+ 1800
      ACCTCTCGCTCCCACGACCGTGCGGACGGAAACGCTCGAGCGTGAGCGGATACTTATAGA
1801  ------------+----------+----------+----------+----------+----------+ 1860
```

FIG. 7B

```
         ACTGTTCTACGGCTACTGTGTAAACGAACGGGGCCTCGACAGCAACGCGTTGAGCCTCGC
    1861 ------------------------------------------------------------ 1920
         CCTCCTCACAGACCTGGAGCTCGTCCAATCGTACCTGGAGTGGCGCGTGAATAGGTACAA
    1921 ------------------------------------------------------------ 1980
         GGACGAGGATTTACCCCCCGTTACTCGATCGGAATACATGTTTATCGCCCTGGTGAAAAA
    1981 ------------------------------------------------------------ 2040
         ACTCCACAGAGGTTATCTCCGCGCCCTTGGGCTTGGGGTAGACCCGGACGGGGTGAAAGA
    2041 ------------------------------------------------------------ 2100
         GCTGGAACGGAAACTGAAAATCGCCGGAATTGATGTCACGGACGGCTACCACGCGGTGGA
    2101 ------------------------------------------------------------ 2160
         GCCCCTCCTGGAAACTCACGAGCCCCTCCGCTGGGTGCTGGATGGCATCCGGCTCATGCT
    2161 ------------------------------------------------------------ 2220
         CCGCGATGCGGCGGGGCGGGTAGGCAACCTGCTGACACCCCAAATCCCCACCGCCAAAAG
    2221 ------------------------------------------------------------ 2280
         CGAAGCGGGCGAAGCGTTCGCCCTCTACCGGGACGTCGTTCTGCTTTGGATGATGGTGGG
    2281 ------------------------------------------------------------ 2340
         CCACCCCTCCGGGCGAAGCATTACTACGAAGCTCGCTTGGACATGAGCCAGTTCCAAGA
    2341 ------------------------------------------------------------ 2400
         CGGGGATTTCGCTCCCGGGCGGGGACACGTGGGCGGGCCGGCGGAGGGTACTACCTGGC
    2401 ------------------------------------------------------------ 2460
         CTACCGCAAAGTGGAGTTCAAAAAACGCCCGAGGCCAGGTCTTTCAGAGCCTCCAGGACCA
    2461 ------------------------------------------------------------ 2520
         CGATCTCGTCACGTTCCCCCTGGACGACCCCGAGCACCCTGTCCTGGTCCTGGACGTGAA
    2521 ------------------------------------------------------------ 2580
         CGGGATGCGGTACTCCCTCAACGAGCTCTTTCACGTCTACCTGCGCACGATCCTCTCCCG
    2581 ------------------------------------------------------------ 2640
         CCTGGCCCAGGCCTGGGCCGGACCGGTCCCCTCCTGCCCCTGTTTCCGGGTGCCGATACG
    2641 ------------------------------------------------------------ 2700
         AGGCTCAGACTTGCGCACATCGTTCGCAGGCGCGCCGCCTACGTGGCCGCCGTGCCCGGG
    2701 ------------------------------------------------------------ 2760
         GTACCCCAGAAACTTTTGCCCTTCGGCCCCCACTCCATCCGCCACGTGGTGGCCACGGAG
    2761 ------------------------------------------------------------ 2820
         GTCGTGAAGCGCACGGGCTCTTTTGAGGCCGCCGCCAACGTGCTCCTGGATAGCATAGAC
    2821 ------------------------------------------------------------ 2880
         ATGGTCGTTCGACATTACGCCCGTTCGTTCCCCGCGACCGTAACAGTCACGGTTGGCGGG
    2881 ------------------------------------------------------------ 2940
         CTAACGCCCGCGCCCGGGGAGGTGAGCGGTGAGGGACCTCCACGACTTTTTCCTGGCCCG
    2941 ------------------------------------------------------------ 3000
         GGTGGACGAACTGGTGCCGGAACTCCTACCCGGGGCGCGGCGGGTGGGCGACGAGTGGCG
    3001 ------------------------------------------------------------ 3060
         GGCGGGCTCGGTCCAGGGCGAGCGGGGCGACAGCCTGGCCGTGGACCGCGGGAAGGGCTT
    3061 ------------------------------------------------------------ 3120
         CTGGATCGACCACAACCCCTCGGCCCCCGAGCCCCGGCAGGGAAACCTCCTCACGCTGAT
    3121 ------------------------------------------------------------ 3180
         CCAGGCGGCCAAGGGGCTCTCCCCCGAGGAGCCCGGCGCTGGGCCCAGCAGTGGCTTGG
    3181 ------------------------------------------------------------ 3240
         CCTCTCCCCTTCGCCAAAGGTCAGGCGGACGAGGAGCTCAGGACCAAAGGTCTTGAGTAC
    3241 ------------------------------------------------------------ 3300
         TCAAGTGCGTGGGAGCTCGGGTGCTCCAGTCCCTGAGTCTTCAGGTTCCCAGGTACCTGA
    3301 ------------------------------------------------------------ 3360
         GGAGTCGGACCCCTTTGACAACCCCCGCTTCCGGGACCTCCTCACCCCCAGGGGCGAGGA
    3361 ------------------------------------------------------------ 3420
         CGAGGCCCCCTTGGCCCCGGCCTCCGAGGAGGTGCTGCGGCGCATGGTGTCTAGGCTTCT
    3421 ------------------------------------------------------------ 3480
         CCGCACCCCCGAGGCCGTGGCCTACCTGAAGGGGCGCGGTCTGGATGCCCGGGTGGTCCG
    3481 ------------------------------------------------------------ 3540
         CCGCTTCTACCTCGGCCTGGACGACACCGCGCGGGCCACCGCCGCCCTGGTCTACCCGGT
    3541 ------------------------------------------------------------ 3600
         GATAGGGCCGGACGGCTCCCCCGTTCGCCGCCACCTCTACTACGAGATCCCCGGCCTCAC
    3601 ------------------------------------------------------------ 3660
         CCAGGGCGCCCCGGGCAAGGGCTGGGGAGGGGGAGGCCCACCAGCTACTGGGCCCTCCC
    3661 ------------------------------------------------------------ 3720
```

FIG. 7C

```
     CCCCTTCGAGGGCCCCTCCCCCCGCCGCAAGCTCTTCTTGTGCGAGGGGGCGAAGGATGC
3721 ---------+---------+---------+---------+---------+---------+ 3780
     CTGGGCCCTCTGGCTCCACCTCCACGCCCAGCCCTGGGCCCAGGACCTGGCGGTGGTGAC
3781 ---------+---------+---------+---------+---------+---------+ 3840
     CTCCACGCACGGCTCCGCCCTCCCCGAGGCCTGGAAAGACCCCCTGTTCTGGGCCCCTTG
3841 ---------+---------+---------+---------+---------+---------+ 3900
     GGAGGAGGTCTACCTGGGCCAGGACGCCGACTCCGCCGGCGAGGAGATGGCCCGGAAGGT
3901 ---------+---------+---------+---------+---------+---------+ 3960
     GCCGGAGGTGGCGAGGCGGCCCGTCCGCCGCGTCCGGGTCCCGGAGGGGATGGGGAAGGA
3961 ---------+---------+---------+---------+---------+---------+ 4020
     CTGGACGGACTACTTCCTGGCGGGGGGCACCCCCGAGGGCTTGCGCCTCCTCCTGGAGGG
4021 ---------+---------+---------+---------+---------+---------+ 4080
     AGCGGAGGTCTGGGAAGAAGAAGTGGCTGGAGGTGGGGCCAGGATCCAGCTCCCGGACCC
4081 ---------+---------+---------+---------+---------+---------+ 4140
     CGTGGACATCCAGCGGGCCTTCGTGCGGGGCCACCTCTACGTCCCCGTGCGGGTCCTGGA
4141 ---------+---------+---------+---------+---------+---------+ 4200
     GAACCGGGGGAAGAAGGGGCCCGCTACCGCACCGTGGTGGTCCGCTCCGACGGGGCCGT
4201 ---------+---------+---------+---------+---------+---------+ 4260
     CCTGGGCTGGGGCTACTTGCCGGCCCCGCCCGGCACCCCCTTGGAGGACCGGGTGCTGGC
4261 ---------+---------+---------+---------+---------+---------+ 4320
     CGTGGACGACGGCACCATCATCCGCAGGCCCCCGAAGGCGGCCGCCGGGACCTCGTGGAA
4321 ---------+---------+---------+---------+---------+---------+ 4380
     CGGGGAGGCCATCAACCGCTTCCTGGAAGCCCGGGCCCGGGGAGTGAGCGCCATGACCGT
4381 ---------+---------+---------+---------+---------+---------+ 4440
     GGCCCCCGGGACCTGCCTGGGCTCATCGTCCGCCACCTCCGCCAGGTGATCCTCCCCAG
4441 ---------+---------+---------+---------+---------+---------+ 4500
     TGAGGACGGCTACCTCCTGGCCGCCTTAGGGGTCATGACCTCCTACGTGCAGAGCGTCTT
4501 ---------+---------+---------+---------+---------+---------+ 4560
     CGACGCCGTGCCCCTCTTCCTCGTGGTGGGCCCGCCGGGCTCGGGGAAGACGGAGTTCGC
4561 ---------+---------+---------+---------+---------+---------+ 4620
     CCGCCTCATGGCCGAGCTGGGGGCCAACGGCGTGGTGATCACCGGCCAGACCTCCGCCGC
4621 ---------+---------+---------+---------+---------+---------+ 4680
     CACCGCCGCCCGGATCATCGACGAGACGGGGGGGCTGGTGGCCTTCGACGACCTGGAGGA
4681 ---------+---------+---------+---------+---------+---------+ 4740
     GGTGCGCCAGCGGTCGGGGAGCGCTGAGGCCTCCCAGCTGGAGCAGTTCCTCAAGGTGTC
4741 ---------+---------+---------+---------+---------+---------+ 4800
     CTACAAGAAGGAGACCGCGGTCAAGAGCTGGACGGACACCAAGGGGATGCGGGTCCTCAC
4801 ---------+---------+---------+---------+---------+---------+ 4860
     CCTCAACTTCTTCGGGGTCAAGGTGATCACCAACACCCAGGGGACGGGGGACATCCTGGG
4861 ---------+---------+---------+---------+---------+---------+ 4920
     GAGCCGGATGCTGGTCATCCGCACCGCCCGCCTCCGGGACCTGGGCAGAGGGGAGGAGCG
4921 ---------+---------+---------+---------+---------+---------+ 4980
     CCGCCCCGAGGGGCTCTCCCCCCCAGGCCCTCCAAGAACTCCGGGACAACCTCTACATCT
4981 ---------+---------+---------+---------+---------+---------+ 5040
     GGGCCATGGAGAACGCGGCCAGCCTCCACGCCCTGTACCGGGAGCGCTTCGCGGGCAAGG
5041 ---------+---------+---------+---------+---------+---------+ 5100
     GGGAGCGCCTGGACGAGATCGCCGCCCCCTTGCGTACCATCGCCCACCACCTGGGGGACG
5101 ---------+---------+---------+---------+---------+---------+ 5160
     AGGAGCTGGCGGCCCGCCTGGAGGACGCCCTGCGCCGGCAGGAAGGGCGCCTGGAGGAGA
5161 ---------+---------+---------+---------+---------+---------+ 5220
     CCCTTTCCGATGCCGAGGTGGTGGAGACCGCCCTCAAGGAGGCCATCCGCCAGGGCTACC
5221 ---------+---------+---------+---------+---------+---------+ 5280
     GGAGCCACGTGGCCCTGGTCCACGTGATCTTCCAGGCCCGGAAGATCTTCGGGGACGACT
5281 ---------+---------+---------+---------+---------+---------+ 5340
     GGGGCCGGGAGCGCACCGTGGACATCCCCCGGTGGCGGGACCCCAAGTGGGTGGGGCAGA
5341 ---------+---------+---------+---------+---------+---------+ 5400
     TCGCCAGCAACTACGGCTGGGCGGCCCCAGAAAAGGCCCGTGAGGCCCCGGCTTTGGGACA
5401 ---------+---------+---------+---------+---------+---------+ 5460
     AGCAGTTCCGCATCATGCGCCTGGAGCCCACCTTCGTGGAGCGGGTGGTCAGGGGCTTCC
5461 ---------+---------+---------+---------+---------+---------+ 5520
     TCCAGGAGGGGATCCCCTTGGAGCCCCTGAAGCAACCCCTGGCTTCTGCCTGGACACCCC
5521 ---------+---------+---------+---------+---------+---------+ 5580
```

FIG. 7D

```
        CTGCGCCGAGTGCGCCTACCTGCACTGGTGCGACCTCCGGCCTGACAAGGAAAAGTGGCT
   5581 ------------+---------+---------+---------+---------+---------+ 5640
        GGAGCGCTACGGGGAGGCCAAGCTGGCCCAGAAAAGGCGGGAGCTGGAGGAGGAGTTTTT
   5641 ------------+---------+---------+---------+---------+---------+ 5700
        GGCCCTGGTGGGGCCCCAAGATGGCCTTGGCCTCCAGGCTTCCGCCGAGGAGGAGGGAGA
   5701 ------------+---------+---------+---------+---------+---------+ 5760
        CCGAGGTAAGCACCCAAGTACCCAAGTACCCAAGACCCTAAAGCCTCAGGTACCGGAGGA
   5761 ------------+---------+---------+---------+---------+---------+ 5820
        CCTCGGGGACGGAGGACCTAAAACCCCAAGGGCGTGAAAGACTGAGGTGAGAGGGATGAT
   5821 ------------+---------+---------+---------+---------+---------+ 5880
        CGTGGCTGTCACCGGCTTCAAGGGAGGGGTGGGGAAGACCACCACGGCGGTCCACCTGGC
   5881 ------------+---------+---------+---------+---------+---------+ 5940
        CTGCTTCCTGGCCGAGCGGGGCCCCACCCTGCTGGTGGACGGGGACCCCAACCGCTCCGC
   5941 ------------+---------+---------+---------+---------+---------+ 6000
        CACGGGGTGGCACCGGAGGGGAGGCCTCCCGGTGACCGTGGTGGACGAGCGGGTGGCGGC
   6001 ------------+---------+---------+---------+---------+---------+ 6060
        CCGGTACGCCCGGGAGCACGCCCACGTGGTCATAGACACCCAGGCCCGCCCCACGGAAGA
   6061 ------------+---------+---------+---------+---------+---------+ 6120
        GGACCTCCGGGCCCTCGCCAAGGGGGTGGACCTGCTGGTCCTGCCCACGTCCCCCGACGC
   6121 ------------+---------+---------+---------+---------+---------+ 6180
        CCTGGCCCTGGAGGCCCTCCTGGCCACCCTGGAAGCCCTGCGGGGGGCGGAGGCCCGCTT
   6181 ------------+---------+---------+---------+---------+---------+ 6240
        CCGGGTCCTCCTGACCATGGTGCCCCCGCCCCGAGCCGGGACGGGGAGGAGGCCCGGGC
   6241 ------------+---------+---------+---------+---------+---------+ 6300
        CCTCTTGGGGGCGGAGGGCGTTCCCCTCTTCACAGGCTGGGTGAGGCGGGCGGCAGCCTT
   6301 ------------+---------+---------+---------+---------+---------+ 6360
        CCCCAAGGCCGCCCTCCTGGGGGTGCCTGTCTACCGGGTGCCCGACCCCAGGGCGAGGCT
   6361 ------------+---------+---------+---------+---------+---------+ 6420
        GGCCTGGGGGGACTACGCGCGGGTGGGGGAAGAGCTCCTGAAGGAGGTGGGGGGATGAGC
   6421 ------------+---------+---------+---------+---------+---------+ 6480
        AAGTTCGCCAGGCTCCTCAAAGAGGTCAAGGAGAAGGAGGAGGCCTCCGGGGAGCGGCCT
   6481 ------------+---------+---------+---------+---------+---------+ 6540
        CGGGGGAAGAGCCGGCGGGAGGACTACGTGGCCATGAAGGTCTACATCAGCAAAGAGCTT
   6541 ------------+---------+---------+---------+---------+---------+ 6600
        CACCGGAGGCTGAAGCTGAAGGCCCTGGAGGAGGAGAAGGAGCTTTCGGAGCTGGTGGAA
   6601 ------------+---------+---------+---------+---------+---------+ 6660
        GAGGCCCTGAGGAAGTTGCTGGTGTGACCTCCTCCCGCCTCGTAGAGCGTGAAAAGGAGG
   6661 ------------+---------+---------+---------+---------+---------+ 6720
        TAAGACGATGGTCACCCTTAACAAATCGCCCCTAGAAGCCCTCTACGCGGGCCACTCCCC
   6721 ------------+---------+---------+---------+---------+---------+ 6780
        CCAGGAGGCGGGCCGTCTCTTCGAAGCGCCTGGTCCGCAAGATATTGAAGGAACTCCACC
   6781 ------------+---------+---------+---------+---------+---------+ 6840
        CCATCTGGAGCCAAGAGTTCGTGGATGTCGTCCCTTGGTCCGAGCACGCCACCCGCAAGG
   6841 ------------+---------+---------+---------+---------+---------+ 6900
        GGCTCAGGGCCACGGACATCGGCGTGGACCTGGTGGGCTACGGGAAGGACGACAAGGTCT
   6901 ------------+---------+---------+---------+---------+---------+ 6960
        ACGCCATCCAGGTCAAGCTGTGGGATAAGCCCCTCTCTTGGAAGGACCTGGGGAGCTTCG
   6961 ------------+---------+---------+---------+---------+---------+ 7020
        TGGGGGTGGTGAACCACCCCGAGTACGGCTTCGACCACGGGCTCATCGTGGCCCCAAGAG
   7021 ------------+---------+---------+---------+---------+---------+ 7080
        GCGTGACCCAGGAGGCCGACCGCCAGCTCCAGGGCCTACCCATCACCATCCTGAGCGAAG
   7081 ------------+---------+---------+---------+---------+---------+ 7140
        AGGCTCTCCTAGAAGACCTGGACCTGGAATCCCTCGTTCCAGACCGCCCCGAGGAAGCCC
   7141 ------------+---------+---------+---------+---------+---------+ 7200
        GCAGGCGGGGAAGAAGGCCCTCCGTAAGTACCAGCAAGAAGCCTTAGAGGAGGTGGCCA
   7201 ------------+---------+---------+---------+---------+---------+ 7260
        AAGCCTTCTTAGAGAAGGGCCTGCCCCGGGGCAAGCTCATCATGCCCCCGGGCACGGGCA
   7261 ------------+---------+---------+---------+---------+---------+ 7320
        AGACCCTGGTGGCCCTCAAGATCGCCGAAAAGGTGGCGGGCCCCGGGGGAGGGTCCTCT
   7321 ------------+---------+---------+---------+---------+---------+ 7380
        TCCTGGCGCCCTCCATCGCCCCTCCTGGACCAGTCCCTCAGGGCCTGGGCGGCGGAGGCTT
   7381 ------------+---------+---------+---------+---------+---------+ 7440
```

FIG. 7E

```
        CCTTGCCCTTGCGCCTCTTCGCCGTGGTCTCGGACACGGGCGTGGGCAAGACCTCGGAGG
7441    ---------+---------+---------+---------+---------+---------+  7500
        ACGACCTCTCCGCCCTCTCCCTCCTCTCCATCCCTCCTACCACCAAGCCTGAGGAGCTGG
7501    ---------+---------+---------+---------+---------+---------+  7560
        CCTCCGAGGCCAAGACGGAGAGTCAGGAGGCCCTCACCGTGGTCTTCTCCACCTACCAGT
7561    ---------+---------+---------+---------+---------+---------+  7620
        CGGCGGAGGTCCTGGAGAGGGCCCAGAAGGAGCACGGGCTTCCCCCTTTTGACCTGATGA
7621    ---------+---------+---------+---------+---------+---------+  7680
        TCCTGGACGAAGCCCACCGCACAGCCACGGTGCGGGCGGGAGAAGAAAGCCCCTTCACCA
7681    ---------+---------+---------+---------+---------+---------+  7740
        AGGTGCACCACGACCACTACGTGAAGGCCCGCCACCGCCTCTACATGACGGCCACGCCCA
7741    ---------+---------+---------+---------+---------+---------+  7800
        GGATCTGGGAGGTGGAGGGGAATGGAGAGAGGGGCCAAGGGAAAAAGGCGGGGAAAAAGA
7801    ---------+---------+---------+---------+---------+---------+  7860
        AGGACCCTCAGAAAGAGGGTTCTCCTCCCCTTTTGGACCTCGGTGCCTCTCCTACGGAGG
7861    ---------+---------+---------+---------+---------+---------+  7920
        ACTCCACGGCCCCCGAAGGGGTGGAACTCCTGGTCTACTCCATGGACAACGAGGGGATCT
7921    ---------+---------+---------+---------+---------+---------+  7980
        ATGGCCCCACCCTCTACGAGTACACCTTCACCCGCGCCGTGAAGGAGGGCCACCTGAGCG
7981    ---------+---------+---------+---------+---------+---------+  8040
        ACTACAAGGTCATCGTCTTCTCCGTGGCGGAGGAAGCCCAAAAGGACCTGGCCTCCTACC
8041    ---------+---------+---------+---------+---------+---------+  8100
        TCCAGGGACCCGAGGCCCTCAAGGTGGAGGAGGCTCTGAAGGCCCTGGGCCTGTGGAAGG
8101    ---------+---------+---------+---------+---------+---------+  8160
        TCCTCCAGGGGGAGGTGCGGGACGAGGAGGGGAACCCGATGGGGGGCCTCGACCTGCGGA
8161    ---------+---------+---------+---------+---------+---------+  8220
        GAGTCATCGCCTTCCACGGCCGGGTGAAGGAGTCCAAGGAGATGGAGGAAGAGTTCACGA
8221    ---------+---------+---------+---------+---------+---------+  8280
        AGGTGGCCCTCGCTGCCCAGCAGGCTGGCCTCCTTCCCGAGGAGCTCCGGCGGGTGGAGG
8281    ---------+---------+---------+---------+---------+---------+  8340
        TGAAGCACATAGACGGGCAGATGTCCGCCTATGACCGGAAGCGCCTCCTGGACTGGCTTA
8341    ---------+---------+---------+---------+---------+---------+  8400
        GGGAGAACGTCCCCGAGGGGGAGGTCCGCCTCCTCACCAACGCCAAGGTCCTCACCGAGG
8401    ---------+---------+---------+---------+---------+---------+  8460
        GGATCGACGTCCCGGCCCTAGATGCCGTGGCCTTCATGCGTCCCCGGGACAGCGTGGTGG
8461    ---------+---------+---------+---------+---------+---------+  8520
        ACGTGATCCAGGCCGTGGGGCGGGCCATGCGCAAGGCCCCGGGCAAGGAGTACGGGTACG
8521    ---------+---------+---------+---------+---------+---------+  8580
        TGGTCCTGCCCGTGGTGGTGAGGGGGCAGGACGAGGAGCGGGAGATCGAGGAGAGCGGCT
8581    ---------+---------+---------+---------+---------+---------+  8640
        ACCGGGCGGTGTGGCAGGTGCTCTCGGCCTTGCGCTCGGTGGACAAGTCCTTCGAGGCCC
8641    ---------+---------+---------+---------+---------+---------+  8700
        GCATGCGGGCCGCCCTGGTGCGCCTCTCGGGTAAGGGCGAGGGCGGGGAAGGTGGAGAGG
8701    ---------+---------+---------+---------+---------+---------+  8760
        CCCGAGAGGGTGTGGCCGTCATCGGGGAAGGAAGCGCCTCCCCCGTGATCGTAGATGTCC
8761    ---------+---------+---------+---------+---------+---------+  8820
        TTCAGGGGAACCTCAACCTCCACCAGGAGATCACCCGGAGCCTCGCCGGCAAGCTGGTCA
8821    ---------+---------+---------+---------+---------+---------+  8880
        GGCGCCTCGCCCTGGGGCGGAAGTACCTGGAGAACTGGGCCCAGGACGTGGCCCGGGTGG
8881    ---------+---------+---------+---------+---------+---------+  8940
        CGAAGGTGCTGGAGCAGCAGGTCAGGGCGATGGCGGAGCGGGACCCCAAGGTGAAGGAAA
8941    ---------+---------+---------+---------+---------+---------+  9000
        AACTGGGGAAACTCCTCGCCGCCCTGCAGGCCTTCACCAGCGAGAGCGTGACGGAGGACG
9001    ---------+---------+---------+---------+---------+---------+  9060
        AAGCCATCCTCATGCTGGTCCAGCACGCTCTCACCAAGCCCATCTTCGACGCCCTCTTCG
9061    ---------+---------+---------+---------+---------+---------+  9120
        GGGAACTCCTAGAAAAGCGGGAGGACCCCGTTTCCCGGCCCTAGACGAACTCTTCCAGG
9121    ---------+---------+---------+---------+---------+---------+  9180
        AGTTCAGGGGGTTCCTGGACCGGGAAGGGGAGGCCCTCAAGGATTTCTACGAAGAGATGC
9181    ---------+---------+---------+---------+---------+---------+  9240
        GCCTCAAGGCCCTAGGGCTCACGGACGAAGCCGAAAGGGCCGACTTCCTACGGAGGCTCT
9241    ---------+---------+---------+---------+---------+---------+  9300
```

FIG. 7F

```
     ACTCCAACTTCTTCGCCCGGGCCTTCCCCCAGGTGGCCGACCAGGTGGGGATCGCCTACA
9301 ------------------------------------------------------------ 9360
     CCCCGGTGGAGCTGGTGGACTTCCTGGTGAAGAGCGCAGACGAGCTGGCCAGGAAGCACT
9361 ------------------------------------------------------------ 9420
     GTTGGCCGGGGGCTCGATGGGGAGAAGGTCTTCATCCTGGAGCCCTTCGCCGGCACAGGC
9421 ------------------------------------------------------------ 9480
     ACCTTCGTCACCCGAATCCTGCACCGGGTAGCCGAAAGGGGCGGGGCCGACGCGGTCAAG
9481 ------------------------------------------------------------ 9540
     GGCAAGCTGGAGCGGGGGGAGATCTGGGCCAACGAGATCCTTCTCCTCCCCTACTACGTC
9541 ------------------------------------------------------------ 9600
     CTCAGGGCCAACGTGGAGAACACCACCCTGGCCCTGACCGGGGAGTACGTCCCCTTCAAG
9601 ------------------------------------------------------------ 9660
     GGGGCGTTCTGGCGGACTCCTTCGGCTGGCGGAGCTGGGGTATAGCGAGAAAAAGTTTGG
9661 ------------------------------------------------------------ 9720
     CATCATCCCGCTCTTCCCGGAAGAATACGGTGAGGCCCTGAACGAGCAGCTGAAGGCCCC
9721 ------------------------------------------------------------ 9780
     TATCCAGGTTATCCTCTCCAACCCCCGTGCGGGCTTGGTTGGAGAAGGAGGGCGAGGGG
9781 ------------------------------------------------------------ 9840
     AAGAAGAACCCCGTCTACCGTAAGGTGCGGGAGCGGGTGGAGCCAACCTATGTACGGCGG
9841 ------------------------------------------------------------ 9900
     GCCAAGGAACTTCCCATCGGGGGGACAAAAACCCAAGGGAGAGAACCTGAACTCCCTCTAC
9901 ------------------------------------------------------------ 9960
     GACCAGTACATCCAGGCCTTGCGGGTGGCGAGCGACCGTATCGGGGAGGAGGGGTCGTG
9961 ------------------------------------------------------------ 10020
      GCCTTCGTCACCAACAACGGGTGGCTGGGGGGCGTAGTGCCCCGGGGCTTGCGGGCCTCT
10021 ------------------------------------------------------------ 10080
      TTGGCGGAGGAGTTCGCCGAGGTGTACGTCTACGACCTGAGGGGGGATGCGAGGGAGAAG
10081 ------------------------------------------------------------ 10140
      GGGGAGGCACGGAAGAAGGAGGGGGGCGGGGTCTTTGGACAGCCTTCCCGCGCCGGGGTC
10141 ------------------------------------------------------------ 10200
      TGCCTCCTCCTCCTGGTGAAGCGTAAGGACCACAAAGGGATCGGCAAGGTCCACCTCTAT
10201 ------------------------------------------------------------ 10260
      CGGGTCGGGGACGGCCTCTCCCGGGAGGCCAAGCTGGCTCTGGTGAAGGAGCATGGCTCA
10261 ------------------------------------------------------------ 10320
      GTCTCTGGGTTCCCTGGCAAGAGGTTCCCTATGAAGAGTGGGTGGGGAGGCTTACCCCCG
10321 ------------------------------------------------------------ 10380
      GGTTCTCGGGGATGTTGTCCCTGGACGAGGTCTTTGAGGTGCGGAGTTCTGGGGTGAAGA
10381 ------------------------------------------------------------ 10440
      CCAACCGCGATGCCTACGTCTTCAACCCCTCCCGGGCGGAGCTGGAGCGGCACATGAGGC
10441 ------------------------------------------------------------ 10500
      GGCTCATCTCCACCTACAACGAGCACGTGAAAAGGAAAAAAGAGGGGAAACTAGGGGAAC
10501 ------------------------------------------------------------ 10560
      TGGAAAAGGATGAGAGCATCATCAAGTGGGATAGGGAACTCATCAGGTACCTAGAGTCCC
10561 ------------------------------------------------------------ 10620
      TGAGGGAAGCTTCCTACGAAGGGAGCGGTCAAGTCTACGAGGCCCTCTACCGCCCCTTCG
10621 ------------------------------------------------------------ 10680
      TGCCTATGTACCTCTACCTCAGCCGCACTTTCAATAGCATGATTTACCAAATCCCCCGCA
10681 ------------------------------------------------------------ 10740
      TCTGGCCCACCCCCGAGGCCGAGAACCTGGCCATCGCCGTGGCCGGAAAGGGGAGTAACG
10741 ------------------------------------------------------------ 10800
      CTTTTAGCGCTGTGGCCACCAGGAGGGTGGTTGACCTGCACTTTATTGAGACCACCCAGC
10801 ------------------------------------------------------------ 10860
      TCTACCCCCTTTACCACTACCCCGAAAACAGCCCTCTGGGGGGACACCCAAAGCGCAAGC
10861 ------------------------------------------------------------ 10920
      TCAACCTCAAGGAGGAGTTCTTGAGGAAGCTTGGGGAGGTCCTCGGCCGCCCCGTTCCCC
10921 ------------------------------------------------------------ 10980
      CCGAGGAGGCCTTCGCTTACATCTACGCCGTGGTGAGCCACCCCCTCTACGCCGAGCGCT
10981 ------------------------------------------------------------ 11040
      TCGCCAAGGACCTCAAGATGGACCTCCCCCGCATTCCCCTCCCCCAAGATCCCGAACTCT
11041 ------------------------------------------------------------ 11100
      TTGCCAGGCTGGTGAAGGCGGGTCAAGAACTCATTCACCTCCACACCGAGTACGAGACCC
11101 ------------------------------------------------------------ 11160
```

FIG. 7G

```
         TGCCCCCCTGGAGCCCAGTCCCCCTTCGGGTGGAAGAGGGAGGCCCGGAGGACCCTACGA
11161    ------+---------+---------+---------+---------+---------+   11220
         GCGCTACCGGGTGGAGCGGATGAGGCTGGACAAGGAGAGGAGGGTTCTCCAGTACAACGA
11221    ------+---------+---------+---------+---------+---------+   11280
         CTGGGTCCGGGTGGAGGGCATCCCCGAGGAGGCCTTCCGCTGGCGCCCCGGGGGGTACTC
11281    ------+---------+---------+---------+---------+---------+   11340
         CCCCTTGGAGTGGATTGGCCGCTTCTGGAAGGTGGAGGAGAAGGTGCCCAAGGGCAGGGG
11341    ------+---------+---------+---------+---------+---------+   11400
         GGAGGCCATCGTCTGGGACCCCAACCTCTTCCTCAAGGAGAAGGGGGAACCCCGTTACCT
11401    ------+---------+---------+---------+---------+---------+   11460
         CCTGGACCTCATCGGGCGGGCGGTCCAGGTGGCCGTGCAGACGGTTGGGATCCACGAGGA
11461    ------+---------+---------+---------+---------+---------+   11520
         GCTGAGAGAAGACGTGGAAGCTCTGCTGGGTTGAGGGGGTGCTGGCCCGCCGTTCTCCCT
11521    ------+---------+---------+---------+---------+---------+   11580
         ACTCCTTTAGGGCCTACCCCTACGATCCAAGCACGGCCCTGGGGGGCGCTCAGGTGGGCA
11581    ------+---------+---------+---------+---------+---------+   11640
         TCCCACGTCCAAGGCCCCGACTTGGGCACCCCATGCTGCGAACTTACAGCCCAAGGGCCT
11641    ------+---------+---------+---------+---------+---------+   11700
         GAAACATTCCCCCCTGCTCACGGGGGAAAGTTCGTGAAGGAAAGAGCAAAGCCTTTTTTA
11701    ------+---------+---------+---------+---------+---------+   11760
         TCGCATCCGGAGAGATGGCGGGGTGGAACTTTTCCCCGAGGACTCCCCCATAGGGACATG
11761    ------+---------+---------+---------+---------+---------+   11820
         TAAACGGCAAGCTATCAGTGTAGACTTTTTTCAAAAAGAGCCATACTCGTGTTTTCCCGT
11821    ------+---------+---------+---------+---------+---------+   11880
         TCAGAACGGCATTTTTGCTAAGGAGGTGGTTTACAAATGGGTGTTAATGCGCTACATCCT
11881    ------+---------+---------+---------+---------+---------+   11940
         CCGGTAGTAGGAGCATGC
11941    ---------+--------   11958
```

METHOD FOR CONSTRUCTION OF THERMUS-E, COLI SHUTTLE VECTORS AND IDENTIFICATION OF TWO THERMUS PLASMID REPLICATION ORIGINS

RELATED APPLICATIONS

This is a Continuation Application of U.S. application Ser. No. 09/134,246 filed Aug. 14, 1998 now U.S. Pat. No. 6,207,377.

BACKGROUND OF THE INVENTION

The present invention relates to recombinant DNA molecules encoding plasmid DNA replication origins in Thermus, as well as to shuttle vectors which contain the same.

Many species of bacteria contain small circular extrachromosomal genetic elements, known as plasmids. Plasmids have been found in a number of bacteria which live in extreme environments, including the thermophiles, which live at high temperatures of more than 55° C. (Munster et al., Appl. Environ. Microbiol. 50:1325–1327 (1985); Kristjansson and Stetter, in 'Thermophilic Bacteria', Kristjansson, ed., p. 1–18 (1992)). However, most thermophile plasmids remain 'cryptic' in that functional genes have not been isolated from them, hence leaving their functional significance speculative (Hishinuma et al., J. Gen. Microbiol. 104:193–199 (1978); Eberhard et al., Plasmid 6:1–6 (1981); Vásquez et al., FEBS Lett. 158:339–342 (1983)). Common genes found in plasmids include those encoding plasmid replication and cellular maintenance, antibiotic resistance, bacteriocin production, sex determination, and other cellular functions (Kornberg and Baker, 'DNA Replication', $2^{nd}$ ed. (1991)).

It is often particularly difficult to cultivate thermophilic bacteria within the laboratory. They require high temperatures and often-unknown environmental conditions for acceptable growth (Kristjansson and Stetter, in 'Thermophilic Bacteria', Kristjansson, ed., p. 1–18 (1992)). However, with the advent of genetic engineering, it is now possible to clone genes from thermophiles into more easily cultivatable laboratory organisms, such as E. coli (Kristjansson, Trends Biotech. 7:349–353 (1989); Coolbear et al., Adv. Biochem. Eng. Biotech. 45:57–98 (1992)). The expression of such genes can be finely controlled within E. coli.

A Thermus-E. coli shuttle vector would be desirable if one needs to have the convenience of cloning in E. coli, isolation of DNA from E. coli for further manipulations and subsequently gene selection and expression in Thermus. Such Thermus-E. coli shuttle vectors could be used to screen, select and express thermostable proteins in Thermus. Using these vectors, a gene could, for example, be mutated within a mesophile, transferred to a thermophile, and then its encoded protein selected for increased thermostability. In this way, mesophile-thermophile shuttle-vectors can be used to conduct directed evolution, or protein engineering, on desirable gene products.

There is commercial incentive to produce thermostable proteins which are usually more thermostable in denaturing conditions then mesophilic counterparts (Wiegel and Ljungdahl, CRC Crit. Rev. Biotech. 3:39–108 (1984); Kristjansson, Trends Biotech. 7:349–353 (1989); Coolbear et al., Adv. Biochem. Eng. Biotech. 45:57–98 (1992)). These thermostable enzymes can also be used in a variety of assays, such as PCR, restriction enzyme-mediated PCR, thermo-cycle DNA sequencing and strand-displacement amplification, in which high temperatures are desirable. The shuttle vectors of the present invention should facilitate production of such thermostable proteins.

SUMMARY OF THE INVENTION

The present invention relates to recombinant DNA molecules encoding plasmid DNA replication origins in Thermus, as well as to shuttle vectors which contain the same.

Mesophile-thermophile shuttle vectors require origins of replication (oris) to be genetically maintained and transferred within each bacterial species. To construct appropriate mesophile-thermophile shuttle-vectors, restriction digested thermophile plasmid DNA fragments were ligated into the mesophilic vector pUC19-Km$^R$ (the thermostable Km$^R$ marker can be selected at 50°–65° C.). Plasmid pUC19 uses the ColEI ori to replicate within E. coli, and does not replicate within the plasmid-accepting thermophile Thermus thermophilus HB27 or HB27 Pro⁻ (Koyama et al., J. Bacteriol. 166:338–340 (1986)). We reasoned that the introduction of plasmid DNA from related Thermus species, which contained a complete thermophilic ori, would confer plasmid replication within HB27.

The thermophilic eubacterium Thermus species YS45 (Raven et al., Nucl. Acids Res. 21:4397 (1993)) contains two cryptic plasmids, and grows between 55° C. and 70° C. These two Thermus plasmids were named pTsp45S and pTsp45L. These plasmids were digested with a variety of restriction endonucleases to produce fragments that can be cloned into pUC19-derived vectors. A pUC19-derived plasmid with a 4.2-kb XbaI fragment of the small plasmid (pTsp45S, 5.8 kb) of YS45 replicated within HB27. Therefore this XbaI fragment must contain a thermophilic ori. Subsequent deletion analysis revealed that only 2.3 kb (an NheI fragment) within the 4.2 kb was necessary for thermophilic plasmid replication, and that it encodes a replication protein (RepT). The repT gene encodes the 341 amino acid protein, RepT, with predicted molecular mass of 38.2 kDa.

A second Thermus plasmid replication origin from pTsp45L was defined within a 9 kb SphI fragment. This fragment encodes a gene (parA) for plasmid replication and partition. It also contains direct repeats of 5' RRCTTTTYYY 3' (SEQ ID NO:1), 5' RRYTTTG 3' (SERQ ID NO:2), and an inverted repeat of

5' TTAACCTTTTTTCAAGAAAAAGAGATAA 3' (SEQ ID NO:3)

3' AATTGGAAAAAAGTT CTTTTTC
TCTATT
(COMPLEMENT OF

SEQ ID NO:3)

The direct repeats and inverted repeats are important for pTsp45L plasmid replication. Deletion of these repeats abolished replication activity in Thermus.

BRIEF DESCRIPTION OF THE FIGURES

FIG. 1 is the DNA sequence (SEQ ID NO:4) of repT gene from pTsp45S and its encoded amino acid sequence.

FIG. 2 is the promotor sequence (SEQ ID NO:5) upstream of repT gene.

FIG. 3 is the entire DNA sequence (SEQ ID NO:6) of Thermus plasmid pTsp45S.

FIG. 4 illustrates the genetic organization of Thermus plasmid pTsp45S. The gene repT encodes RepT for plasmid replication.

FIG. 5 is the parA DNA sequence from pTsp45L and the encoded amino acid sequence (SEQ ID NO:7).

FIG. 7 is the entire DNA sequence of *Thermus* plasmid pTsp45L (SEQ ID NO:8).

DETAILED DESCRIPTION OF THE INVENTION

Figure 6:
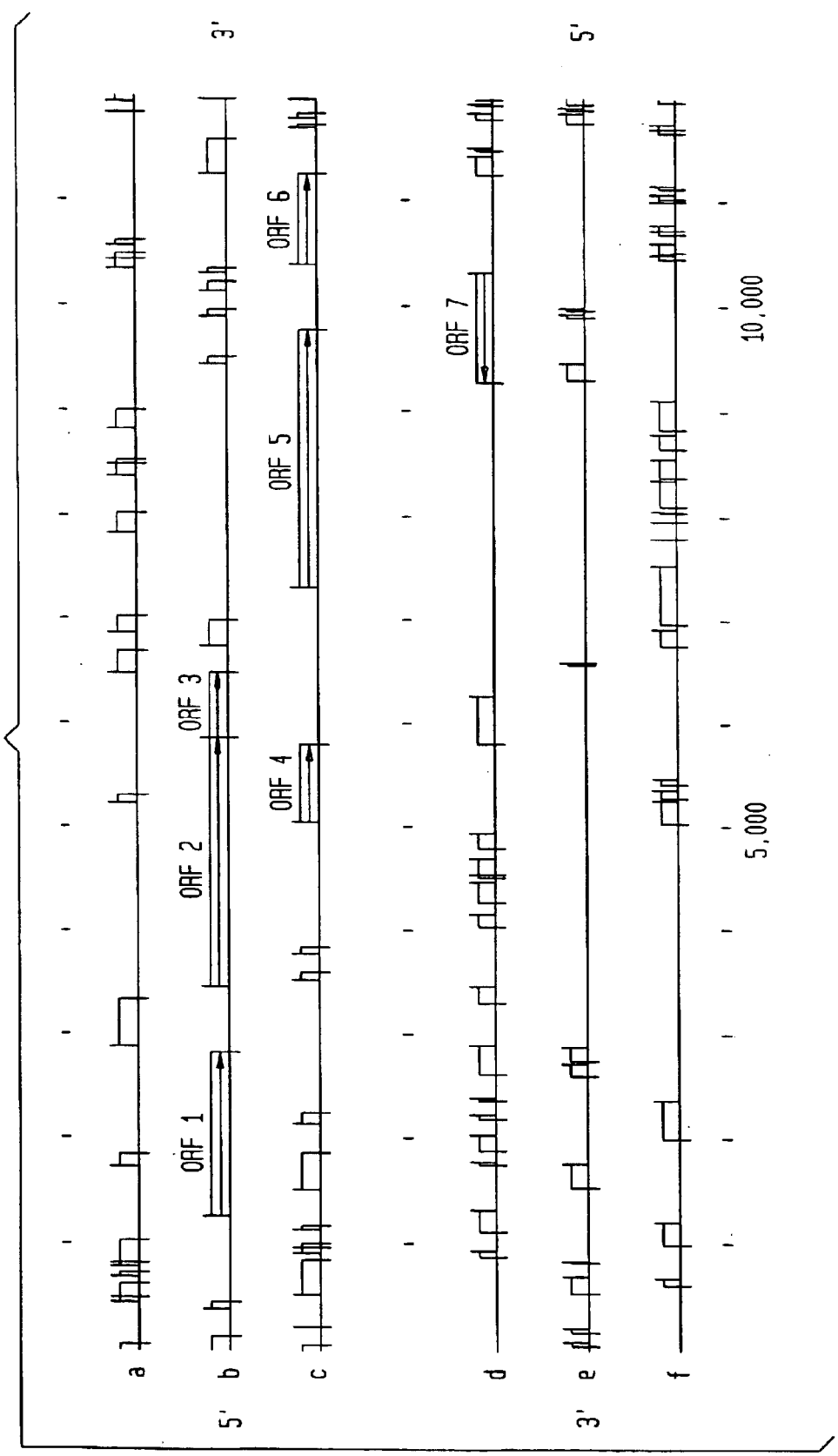
FIG. 6 is the seven open reading frames encoded by pTsp45L. Frames a, b, and c are encoded by the top strand. Frames d, e, and f are encoded by the bottom strand.

The method described herein by which a *Thermus* plasmid replication origin is preferably cloned and selected comprises the following steps:

1. The plasmid DNA of a target host, such as *Thermus* species YS45 plasmid pTsp45S and pTsp45L, is purified.

2. The plasmid DNA is digested with appropriate restriction endonucleases; for *Thermus* species YS45, HindIII, KpnI, PstI, SphI, and XbaI are used to generate 1 to 12 kb restriction fragments. This map is used to orient and localize genes within the plasmid.

3. The digested plasmid DNA is then ligated into similarly cleaved/CIP treated vectors such as pUC-EKR or pUC-EKF ($Ap^R$ at 37° C., $Km^R$ at 50–65° C.) cloning vectors. The ligated DNA is used to transform an appropriate host, e.g., a HsdR$^-$, McrBC$^-$, Mrr$^-$ strain, such as *E. coli* strain RR1. The DNA/cell mixtures are then plated on ampicillin selective media to grow only transformed cells to form primary restriction libraries, such as HindIII, KpnI, PstI, SphI, and XbaI DNA libraries for *Thermus* species YS45.

4. The recombinant plasmids are purified to form the primary plasmid library that might contain thermophilic plasmid origins. Plasmids are digested in vitro with a variety of endonucleases to confirm DNA inserts.

5. The plasmid DNA libraries are used to transform an appropriate thermophilic host cell such as *Thermus thermophilus* HB27 (Pro$^-$) cells and transformants are selected on Km plates at 60°–65° C. for 48 hours.

6. Individual $Km^R$ transformants are amplified in small culture at 65° C. and plasmid DNA is isolated from the overnight cell culture. The plasmid DNA is then digested with an appropriate restriction endonuclease (e.g., HindIII, KpnI, PstI, SphI, or XbaI) to cut out the *Thermus* DNA insert.

7. One clone from the XbaI library described above contained a 4.2 kb *Thermus* DNA which replicates in both *Thermus* and *E. coli*. The 4.2 kb insert DNA of the recombinant pUC-EKF clone was sequenced. To facilitate sequencing, the insert DNA wass further sub-cloned within pUC19 based upon preliminary sequence and mapping. The sequenced DNA was then assembled to match that of the thermophilic plasmid map. The remaining DNA fragments from pTsp45S were also cloned and sequenced. In this way, the thermophilic plasmid (pTsp45S) was completely sequenced.

8. To reduce the size of the *Thermus* replication origin, the 4.2 kb XbaI fragment was further digested with restriction enzymes and subcloned into pUC-EKF or pUC-EKR. One recombinant plasmid contained a 2.3 kb NheI fragment that replicates in *Thermus* and *E. coli*. This plasmid pUC-EKF-Tsp3 is a *Thermus-E. coli* shuttle vector.

9. One open reading frame of 1026 bp encoding a 341-amino acid protein was found within the *Thermus* origin. Deletion of 234 bp (78 amino acid residues) within this gene abolished the *Thermus* replication function. Insertion of stop codons within this gene causes premature termination and negates the *Thermus* transformation. Therefore it was determined that this gene (repT) is required for plasmid replication in *Thermus* HB27 (Pro$^-$) cells.

10. Two *Thermus* promoters were found upstream of the repT gene that are important for repT expression.

11. Plasmid pTsp45L (a mixture of pTsp45L and pTsp45S) was digested with HindIII, KpnI, PstI, SphI, or XbaI. The digested DNA fragments were cloned into pUC-EKR vector to produce *Thermus* DNA libraries for subsequent selection of *Thermus* plasmid replication origin(s).

12. Approximately 450 $Ap^R$ transformants were derived from pUC-EKR+HindIII fragments, +KpnI fragments, +PstI fragments, +SphI fragments, and +XbaI fragments, respectively. pUC-EKR plasmids with HindIII, KpnI, PstI, SphI, or XbaI fragment inserts were amplified in *E.coli*.

13. The DNA libraries were used to transform *Thermus thermophilus* HB27 (Pro$^-$). Transformants were plated on Km plates and incubated at 60° C. for two days. Plasmid DNA was extracted from seventeen $Km^R$ transformants and digested with XbaI, PstI, or SphI. Restriction mapping and Southern blot analysis were carried out.

14. The 9 kb SphI *Thermus* origin insert and the 12 kb *Thermus* origin insert were from pTsp45L. The entire pTsp45L plasmid can be separated into two SphI fragments, 3 kb and 9 kb respectively. The 9 kb SphI fragment contains the functional *Thermus* replication origin. The inserts were sequenced by using pUC19 universal forward and reverse primers and by primer walking. Plasmid pTsp45L is 11958 bp, encoding 7 possible genes.

15. Orf3 is most likely the candidate for pTsp45L replication protein, because it has homolgy to RepA protein of *Agrobacterium* plasmid pTiB6S3, replication protein of *Agrobacterium* plasmid pRiA4b, plasmid partition protein of *Borrelia*, partition protein of *Frankia*, RepA protein of *Rhizobium*, and DNA partition protein ParA of *Caulobacter*. Orf2 may be an accessary protein for pTsp45L plasmid replication. Orf3 was renamed as parA gene.

16. There are direct repeats and inverted repeats in the 9 kb SphI fragment containing the functional replication origin. The direct repeats I are:

| | |
|---|---|
| 5' GGCTTTTCTT 3' | (SEQ ID NO:9) |
| 5' AACTTTTCCC 3' | (SEQ ID NO:10) |
| 5' GACTTTTTTC 3' | (SEQ ID NO:11) | consensus

| | |
|---|---|
| 5' RRCTTTTYYY 3' | (SEQ ID NO:1) |

The direct repeats II are:

| | |
|---|---|
| 5' AACTTTG 3' | (SEQ ID NO:12) |
| 5' AGTTTTG 3' | (SEQ ID NO:13) |
| 5' GATTTTG 3' | (SEQ ID NO:14) |
| 5' AACTTTG 3' | (SEQ ID NO:15) | consensus

| | |
|---|---|
| 5' RRYTTTG 3' | (SEQ ID NO:2) |

The inverted repeat is:

5' <u>TTAACCTTTTTTC</u>AAGAAAAAGAGATAA 3' (SEQ ID NO:3)

3' AATTGGAAAAAAGTT <u>CTTTTTCT</u>
    CTATT 5'                  (COMPLEMENT OF SEQ ID NO:3)

(underlined bases are inverted repeat).

Deletion of these repeats in a HindIII fragment abolished DNA replication in *Thermus*.

Any *Thermus* plasmid DNA, *Thermus* viral DNA, or genomic DNA can be digested with restriction enzymes to generate 2–20 kb fragments. The restriction fragments can be ligated with similarly-cut pUC-EKF or pUC-EKR and transformed into *Thermus* cells and selected for Km$^R$ transformants. Alternatively, DNA can be extracted from environmental samples, such as water from hot springs and soil sediment from hot springs, digested with restriction enzymes, ligated into similarly-cut pUC-EKF or pUC-EKR and transformed into *Thermus* cells and selected for Km$^R$ transformants. Because of the small amount of DNA from environmental samples, one can transfer such DNA into *E. coli* first to amplify the DNA library and then transform such DNA into *Thermus*.

The following Examples are given to illustrate embodiments of the present invention, as it is presently preferred to practice. It will be understood that these Examples are illustrative, and that the invention is not to be considered as restricted thereto except as indicated in the appended claims.

The references cited above and below are herein incorporated by reference.

EXAMPLE I

1. Cloning of a Replication Origin from a *Thermus* Plasmid pTsp45S Native to *Thermus* Species YS45

*Thermus* species YS45 (Raven et al., *Nucl. Acids Res.* 21:4397 (1993) obtained from R. A. D. Williams of Queen Mary and Westerfield College, University of London) can be grown in modified *Thermus thermophilus* liquid media (Oshima and Imahori, *J. Sys. Bacteriol.* 24:102–112 (1974)) consisting of 0.5% tryptone (DIFCO Laboratories; Detroit, Mich.), 0.4% yeast extract (DIFCO Laboratories; Detroit, Mich.), 0.2% NaCl at pH 7.5. Cells are plated in this media with 3% agar. Plated colonies are distinguishable after two days incubation at 55°–70° C. Individual colonies form dense liquid overnight cultures (3–10 ml) at 55°–70° C. in a shaking waterbath. One-ml aliquots of overnight cultures are pelleted and stored at −20° C. for up to one month without loss of viability. Overnight cultures are also stably maintained in media with 25% glycerol at −70° C.

Ten ml of 70° C. overnight YS45 culture is diluted 1:1000 in 500 ml of *Thermus* media, and grown overnight at 70° C. to generate plasmid DNA. Plasmid DNA is prepared via the Qiagen mid-prep protocol (Qiagen, Inc.; Studio City, Calif.) with the addition of 2 mg lysozyme per ml. Lysis is very inefficient without the presence of lysozyme in the first resuspension buffer (Oshima and Imahori, *J. Sys. Bacteriol.* 24:102–112 (1974)). Routinely, between 50–150 μg of plasmid DNA is obtained from 500 ml of overnight YS45 culture.

YS45 contains two plasmids of 5.8 kb (pTsp45S) and approximately 12 kb (pTsp45L) (Wayne and Xu, *Gene* 195:321–328 (1997)). Each plasmid contains a single PstI site useful for linearizing and visualizing the plasmids on agarose gels. Plasmid pTsp45S also contains two XbaI sites that generate 4.2 and 1.6-kb fragments. This plasmid is extensively mapped and cloned into pUC19 as three fragments: 4.2-kb XbaI-XbaI, 0.7-kb XbaI-PstI, and 0.9-kb PstI-XbaI. The 4.2-kb fragment is then further mapped and sub-cloned into pUC19 as six smaller fragments: 0.4-kb XbaI-HindIII, 1.1-kb HindIII-HindIII, 0.7-kb HindIII-HindIII, 0.5-kb HindIII-ScaI, 1.0-kb ScaI-ScaI, and 0.5-kb ScaI-XbaI. Cloning was accomplished by isolating digested fragments from agarose gels and combining them with compatibly cut pUC19 by standard methods (Sambrook et al., 'Molecular Cloning A Laboratory Manual', 2$^{nd}$ ed. (1989)).

The clones are sequenced using universal and reverse M13/pUC primers (New England Biolabs, Inc.; Beverly, Mass.). Preliminary sequencing was used to generate 12 additional primers (synthesized at New England Biolabs, Inc.; Beverly, Mass.) to refine and correct sequencing errors. The primers (shown as top and bottom strand pairs) are:

| | |
|---|---|
| 5'-GGTTCCATAAGGCGGGTCAATATAG-3' | (SEQ ID NO:16); |
| 5'-CTATATTGACCCGCCTTATGGAACC-3' | (SEQ ID NO:17); |
| 5'-GT GGGGTGGGCTGATCAAGA ATCTCCT-3' | (SEQ ID NO:18); |
| 5'-AGGAGATTCTTGATCAGCCCACCCCAC-3' | (SEQ ID NO:19); |
| 5'-TCACCCACAACCCTCACGCACTCCAA-3' | (SEQ ID NO:20); |
| 5'-TTGGAGTGCGTGAGGGTTGTGGGTGA-3' | (SEQ ID NO:21); |
| 5'-AGATGTAGTCGTCCAGGGTGAGCCTG-3' | (SEQ ID NO:22); |
| 5'-CAGGCTCACCCTGGACGACTACATCT-3' | (SEQ ID NO:23); |
| 5'-TTGGTATGTAAAGCCCTTCGCGAGG-3' | (SEQ ID NO:24); |
| 5'-CCTCGCGAAGGGCTTTACATACCAA-3' | (SEQ ID NO:25); |
| 5'-TAGTGGCATCGGTGTTGTCGTGGGT-3' | (SEQ ID NO:26); | and

| | |
|---|---|
| 5'-ACCCACGACAACACCGATGCCACTA-3' | (SEQ ID NO:27) |

(underlined bases are in pTsp45s, but were not originally synthesized in these primers).

2. Characteristics of a Thermophilic Plasmid ori

The 2.3-kb NheI-bounded thermophilic ori is 57% G+C. The 5.8-kb *Thermus* plasmid pTsp45S is 54% G+C, and there are no other published reports of the G+C content in its natural host, YS45. There are no significant AT-rich regions within the sequenced ori.

The thermophilic ori contained one significant ORF of 1026 bp, beginning with GTG and ending with TGA (FIG. 1). The ORFs 341 amino acid could encode a protein with a predicted molecular weight of 38.2 kDa. Centered 10 bp 5' of this ORF is a putative RBS, GGAGG (Hartmann and Erdmann, *J. Bacteriol.*, 171:2933–2941 (1989)). Further upstream, two possible promoter regions (−10 TATTTT, −35, TTGCCA, 17 bp spacing; or −10 TAGGGT, −35 TTGCCC, 18 bp spacing) were found (FIG. 2) with significant homology to the *Thermus* consensus promoter (Maseda and Hoshino *FEMS Microbiol. Lett.* 128:127–134 (1985)). Database searches (FASTA, BLAST) did not reveal any significant homologies to the predicted protein, or to other possible reading frames.

To test the importance of this ORF in the thermophilic replication, a significant portion of it was deleted. Briefly, pUC-EKF-Tsp3 was digested with NruI+PshAI, removing 234 bp or 78 aa within the ORF. The linearized plasmid was self-ligated, generating pUC-EKF-Tsp3-ΔNP(7.5 kb), then amplified in *E. coli* and used to transform HB27. No pUC-EKF-Tsp3-ΔNP(7.5 kb) Km$^R$ transformants were found. It was concluded that 234 bp deletion within the repT gene abolished the replication function. Similarly, the addition of an XbaI amber stop linker (CTAGTCTAGACTAG (SEQ ID NO:28)) at either the NruI or PshAI site of pUC-EKF-Tsp3 negated thermophilic transformation. This indicated that the repT within the NheI fragment was necessary for replication in the thermophile. We suggest that this ORF of pTsp45S is a novel replication protein (RepT) needed for thermophilic plasmid replication. In addition, analysis of this thermophilic ori revealed two sequences with significant homology to highly conserved DnaA boxes.

Although not yet described in *Thermus*, DnaA boxes are required for binding of a DnaA protein, and for subsequent replication of some plasmids (McMacken, et al., DNA Replication (Chapter 39), pages 586–587 in *Escherichia coli* and *Salmonella typhimmarium*, American Society for Microbiology, Washington, D.C.). Both putative DnaA boxes (TTATCACCC (SEQ ID NO:29), TTATCCGAG (SEQ ID NO:30)) of pUC-EKF-Tsp3 lie within the 3' end of repT, and are not within the region deleted in pUC-EKF-Tsp3-ΔNP. Plasmid copy number might be regulated by the relationship between binding of a DnaA homologue at these sites, and transcription of repT.

A sample of ER2688[pUC-EKF-Tsp3] has been deposited under the terms and conditions of the Budapest Treaty at the American Type Culture Collection on Jun. 22, 1998, 1998 and received ATCC Accession No. 98793.

EXAMPLE II

*Thermus* YS45 strain contains two plasmids of 5.8 kb (pTsp45S) and approximately 12 kb (pTsp45L) (Wayne and Xu, *Gene* 195:321–328 (1997)). Each plasmid contains a single PstI site useful for linearizing and visualizing the plasmids on agarose gels. The two plasmid mixture was digested with HindIII, KpnI, PstI, SphI, or XbaI. The digested DNA fragments were cloned into pUC-EKR vector to produce *Thermus* DNA libraries and for subsequent selection of *Thermus* plasmid replication origin(s). Approximately 100, 100, 100, 100, and 50 Ap$^R$ transformants were derived from pUC-EKR+HindIII fragments, +KpnI fragments, +PstI fragments, +SphI fragments, and +XbaI fragments, respectively. Plasmids pUG-EKR with HindIII, KpnI, PstI, SphI, or XbaI fragment inserts were amplified in *E. coli* and the DNA libraries were used to transform *Thermus thermophilus* HB27 (Pro$^-$). Transformants were plated on Km plates and incubated at 60° C. for two days. Plasmid DNA was extracted from seventeen Km$^R$ transformants and digested with XbaI, PstI, or SphI. Restriction mapping and Southern blot analysis indicated that the 4.2 kb XbaI fragment *Thermus* origin insert was from pTsp45S, the 9 kb SphI *Thermus* origin insert and the 12 kb *Thermus* origin insert were from pTsp45L. It was concluded that the entire pTsp45L plasmid can be separated into two SphI fragments, 3 kb and 9 kb respectively. The 9 kb SphI fragment contains the functional *Thermus* replication origin. The two SphI fragments were sequenced by subcloning of one BamHI fragment (1.4 kb), one HindIII fragment (1.9 kb), one SphI fragment (3 kb), two KpnI fragments (2.5 kb, 0.6 kb), three SacI fragments (4.3 kb, 1.9 kb, 1.3 kb), and multiple SmaI fragments into pUC19. The inserts were sequenced by using pUC19 universal forward and reverse primers and by primer walking. Plasmid pTsp45L is 11958 bp, encoding 7 possible genes. These seven genes are named orf1 through orf7 (FIG. 6). Orf1 amino acid sequence has weak similarity to transposases. Orf3 amino acid sequence has similarity to DNA replication protein RepA and DNA partition protein ParA. Orf4 amino acid sequence has similarity to serine carboxy peptidase III. Orf5 amino acid sequence has similarity to UvrB protein. Orf2, orf6, and orf7 amino acid sequences have no homologs to proteins in Genbank. The 3 kb SphI fragment contains orf5 C-terminus portion, orf6 and orf7. Deletion of this 3 kb did not affect pTsp45L plasmid origin of replication. It was concluded that orfs 5, 6, and 7 are not required for plasmid replication. The 9 kb SphI fragment contains the functional replication origin, which contains orf1, 2, 3, 4 and a portion of orf5. Orf1 and orf4 have homology to transposases and proteases, respectively. It was concluded that orf1 and orf4 are unlikely involved in DNA replication and that orf3 is most likely the candidate for pTsp45L replication protein, because it has homolgy to RepA protein of *Agrobacterium* plasmid pTiB6S3, replication protein of *Agrobacterium* plasmid pRiA4b, plasmid partition protein of *Borrelia*, partition protein of *Frankia*, RepA protein of *Rhizobium*, and DNA partition protein ParA of *Caulobacter*. Orf2 may be an accessary protein for pTsp45L plasmid replication. Orf3 (coordinate 5876 to 6478) was renamed as parA gene. The DNA sequence and amino acid sequence of parA is shown in FIG. 5. The location, direction, and organization of the seven open reading frames in pTsp45L are shown in FIG. 6.

There are direct repeats and inverted repeats in the 9 kb SphI fragment containing the functional replication origin. The direct repeats I are:

| | |
|---|---|
| 5' GGCTTTTCTT 3' | (SEQ ID NO:9) |
| 5' AACTTTTCCC 3' | (SEQ ID NO:10) |
| 5' GACTTTTTTC 3' | (SEQ ID NO:11) | consensus

| | |
|---|---|
| 5' RRCTTTTYYY 3' | (SEQ ID NO:1) |

The direct repeats II are:

| | |
|---|---|
| 5' AACTTTG 3' | (SEQ ID NO:12) |
| 5' AGTTTTG 3' | (SEQ ID NO:13) |
| 5' GATTTTG 3' | :(SEQ ID NO:14) |
| 5' AACTTTG 3' | (SEQ ID NO:15) | consensus

| | |
|---|---|
| 5' RRYTTTG 3' | :(SEQ ID NO:2) |

The inverted repeat is:

5' TTAACCTTTTTTCAAGAAAAAGAGATAA 3' (SEQ ID NO:3)

3' AATTGGAAAAAAGTT CTT
    TTTCTCTATT 5'    (COMPLEMENT OF SEQ ID NO:3)

(underlined bases are inverted repeats).

The repeats and inverted repeats are important for pTsp45L origin of replication, because deletion of these repeats in a HindIII fragment abolished DNA replication in *Thermus*. The DNA sequence of pTsp45L is shown in FIG. 7. The *Thermus-E. coli* shuttle vector containing pTsp45L DNA replication origin was named as pUC-EKR-Tsp45L9Kb.

A sample of ER2688[pUC-EKR-Tsp45L9 kb] has been deposited under the terms and conditions of the Budapest Treaty at the American Type Culture Collection on Jun. 22, 1998, and received ATCC Accession No. 98794.

EXAMPLE III

*Thermus* strain YS45 (Raven, et al., *Nucl. Acids Res.* 21:4397 (1993) obtained from R. A. D. Williams of Queen Mary and Westerfield College, University of London) also harbors a plasmid. Plasmid DNA was extracted from *Thermus* species YS45 by midi Qiagen column. The plasmid DNA was cleaved with HindIII, KpnI, PstI, SphI, or XbaI. The digested DNA fragments were cloned into pUC-EKR vector to produce *Thermus* DNA libraries and for subsequent selection of *Thermus* plasmid replication origin(s). Approximately 50 to 300 Ap$^R$ *E. coli* transformants were derived from pUC-EKR+HindIII fragments, +KpnI fragments, +PstI fragments, +SphI fragments, and +XbaI fragments, respectively. Plasmids pUC-EKR with HindIII, KpnI, PstI, SphI, and XbaI fragment inserts were amplified in *E. coli* and the DNA libraries were used to transform *Thermus thermophilus* HB27 (Pro⁻). Transformants were plated on Km plates and incubated at 60° C. for two days. *Thermus* transformants were found in HindIII and PstI DNA libraries. Plasmid DNA was extracted from seventeen $Km^R$ *Thermus* transformants and digested with HindIII or PstI. It was found that the functional Tse plasmid replication origin was contained in a ~7 kb HindIII or PstI fragment. The shuttle vector was named pUC-EKR-Tse7Kb.

EXAMPLE IV

*Thermus* cells can be grown in modified *Thermus thermophilus* liquid media (Oshima and Imahori, *J. Sys. Bacteriol.* 24:102–112 (1974)) consisting of 0.5% tryptone (DIFCO Laboratories; Detroit, Mich.), 0.4% yeast extract (DIFCO Laboratories; Detroit, Mich.), 0.2% NaCl at pH 7.5. *Thermus* cells can also be cultured in 4 to 10-fold diluted rich both at 50°–75° C. Ten ml of overnight cell culture is diluted 1:1000 in 500 ml of *Thermus* media, and grown overnight at 50°–75° C. to generate plasmid DNA. Plasmid DNA can be prepared via the Qiagen midi/maxi-prep protocol (Qiagen, Inc.; Studi City, Calif.) with the addition of 2 mg lysozyme per ml or any other plasmid preparation method such as alkaline lysis or boiling methods. The purified plasmid DNA can be digested with restriction enzymes to produce DNA fragments of 2 to 20 kb. The plasmid DNA can also be sonicated to produce blunt end framgents and be made into sticky ends by addition of deoxynucleotides by terminal nucleotide transferase. The DNA fragments can be cloned into pUC-EKF or pUC19-EKR and the ligated DNA can be used for thermophilic transformation into *Thermus* cells. Transformants can be selected by plating cells on Km plates. Any $Km^R$ transformants should contain *Thermus* plasmid replication origin. The origin can be further subcloned and sequenced. A minimal replication origin can be defined by suboloning smaller DNA fragments into pUC-EKF or pUC19-EKR and the resulting plasmid DNA can be used for thermophilic transformation.

Alternatively, plasmid DNA, *Thermus* viral DNA or genomic DNA can be extracted from environmental samples such as water from hot springs and soil sediment from hot springs and digested with restriction enzymes and ligated into similarly-cut pUC-EKF or pUC-EKR. The ligated DNA can be transformed into *Thermus* cells and select for $Km^R$ transformants. Because of the small amount of DNA from environment samples, one can transfer DNA into *E. coli* first to amplify DNA library and then transform into *Thermus*. The thermophilic replication origin can be further subcloned and sequenced. A minimal replication origin can defined by subcloning smaller DNA fragments into pUC-EKF or pUC19-EKR and the resulting plasmid DNA can be used for thermophilic transformation.

What is claimed is:

1. An isolated DNA encoding a *Thermus* sp. plasmid replication protein, the isolated DNA having a sequence corresponding to SEQ ID NO:4, or variants of SEQ ID NO:4 which encode conservatively modified variants of the plasmid replication protein.

2. A recombinant plasmid comprising the isolated DNA of claim 1.

3. The recombinant plasmid of claim 2, further comprising at least one promoter sequence selected from the group of DNA sequences of SEQ ID NO:6 consisting of residues 27–32 of SEQ ID NO:6, residues 50–55 of SEQ ID NO:6, residues 86–90 of SEQ ID NO:6 and residues 109–114 of SEQ ID NO:6.

* * * * *

SEQUENCE LISTING

```
<160> NUMBER OF SEQ ID NOS: 30

<210> SEQ ID NO 1
<211> LENGTH: 10
<212> TYPE: DNA
<213> ORGANISM: Thermus sp.

<400> SEQUENCE: 1 rrcttttyyy                                                          10

<210> SEQ ID NO 2
<211> LENGTH: 7
<212> TYPE: DNA
<213> ORGANISM: Thermus sp.

<400> SEQUENCE: 2 rrytttg                                                              7

<210> SEQ ID NO 3
<211> LENGTH: 28
<212> TYPE: DNA
<213> ORGANISM: Thermus sp.

<400> SEQUENCE: 3
ttaacctttt ttcaagaaaa agagataa                                      28

<210> SEQ ID NO 4
<211> LENGTH: 1026
<212> TYPE: DNA
<213> ORGANISM: Thermus sp.
<220> FEATURE:
<221> NAME/KEY: CDS
<222> LOCATION: (1)..(1023)
```

<400> SEQUENCE: 4

```
gtg aag aac gaa aaa acc ttc ttt gaa gag ctt tac gag gct tta gag      48
Met Lys Asn Glu Lys Thr Phe Phe Glu Glu Leu Tyr Glu Ala Leu Glu
 1               5                  10                  15 gaa acc cac gac aac acc gat gcc act agg ggg tca gat agg ggg tca      96
Glu Thr His Asp Asn Thr Asp Ala Thr Arg Gly Ser Asp Arg Gly Ser
             20                  25                  30 gag gac ttc ttc ttg gcc acc gac ccc cct cca gat gga ggt gcc gaa     144
Glu Asp Phe Phe Leu Ala Thr Asp Pro Pro Pro Asp Gly Gly Ala Glu
         35                  40                  45 aat cgc ctc gcg aag ggc ttt aca tac caa aaa gag gca ctt agg att     192
Asn Arg Leu Ala Lys Gly Phe Thr Tyr Gln Lys Glu Ala Leu Arg Ile
     50                  55                  60 gct tta ccc gag aaa gac cat gag gct ttc ctt tcc tct gtt ggg gcc     240
Ala Leu Pro Glu Lys Asp His Glu Ala Phe Leu Ser Ser Val Gly Ala
 65                  70                  75                  80 ccc cct ata cca cca gct gaa ccc ccc gtt ggg aat gta tgt caa gcc     288
Pro Pro Ile Pro Pro Ala Glu Pro Pro Val Gly Asn Val Cys Gln Ala
                 85                  90                  95 gtc cag gac ggg cct cag aag ctt ctg gaa ctc ctc cag gag att gcc     336
Val Gln Asp Gly Pro Gln Lys Leu Leu Glu Leu Leu Gln Glu Ile Ala
            100                 105                 110 cgc tcc acc atc ccc tac ggc aac cgg gag ctc tgg agg aag gtg ggg     384
Arg Ser Thr Ile Pro Tyr Gly Asn Arg Glu Leu Trp Arg Lys Val Gly
        115                 120                 125 acg gtc gtc ttc atg gtc ccc ctg gag atg ttg gcc ctc aac ctg ggg     432
Thr Val Val Phe Met Val Pro Leu Glu Met Leu Ala Leu Asn Leu Gly
    130                 135                 140 gtc acc cgg cag acc gtc cac gcc tgg aag aag gtc ctt gag aaa aag     480
Val Thr Arg Gln Thr Val His Ala Trp Lys Lys Val Leu Glu Lys Lys
145                 150                 155                 160 ggc ctg gtg gcc acc gac gtc ctt cac caa acc gtc aac ggg gag cgc     528
Gly Leu Val Ala Thr Asp Val Leu His Gln Thr Val Asn Gly Glu Arg
                165                 170                 175 cgg gcc atc ggc acc ctt tgg gcc gtc cgg ctg agg cca ggg aaa gcc     576
Arg Ala Ile Gly Thr Leu Trp Ala Val Arg Leu Arg Pro Gly Lys Ala
            180                 185                 190 agg ctc acc ctg gac gac tac atc tac ccc tgg agg aac ctc gcc cta     624
Arg Leu Thr Leu Asp Asp Tyr Ile Tyr Pro Trp Arg Asn Leu Ala Leu
        195                 200                 205 gac atg gcc aac ggc gtg ctc tcc ttc aac tgg gtc aag gcc tac cag     672
Asp Met Ala Asn Gly Val Leu Ser Phe Asn Trp Val Lys Ala Tyr Gln
    210                 215                 220 gac cac gga atc cgc ccc acc ctg gac gtg ctg gtc ctc tgg gct cag     720
Asp His Gly Ile Arg Pro Thr Leu Asp Val Leu Val Leu Trp Ala Gln
225                 230                 235                 240 ggg aaa agg gtg atg ccc aac acc aag acc gtg gcc gtt gac ctg ggc     768
Gly Lys Arg Val Met Pro Asn Thr Lys Thr Val Ala Val Asp Leu Gly
                245                 250                 255 ctc atc ctg gtc ctc ccc gag gtg gag cgt tcc aaa ctc ccg gcc ctt     816
Leu Ile Leu Val Leu Pro Glu Val Glu Arg Ser Lys Leu Pro Ala Leu
            260                 265                 270 atc acc ctc att gct acg tac att gcc gat ctc cta gat gac cgt cgt     864
Ile Thr Leu Ile Ala Thr Tyr Ile Ala Asp Leu Leu Asp Asp Arg Arg
        275                 280                 285 tca aga cgt ttc tat gca ggc ttg ctg tgg gct gtg gcc agg ggt gaa     912
Ser Arg Arg Phe Tyr Ala Gly Leu Leu Trp Ala Val Ala Arg Gly Glu
    290                 295                 300
```

```
ctc ccc gcg caa tat cta ttt gcc gtc cta atg cgg gtt atc cga gat      960
Leu Pro Ala Gln Tyr Leu Phe Ala Val Leu Met Arg Val Ile Arg Asp
305                 310                 315                 320 tac acg gat ggc cat ctg aca cga ccg gga gcg tac cta gtg aag acc     1008
Tyr Thr Asp Gly His Leu Thr Arg Pro Gly Ala Tyr Leu Val Lys Thr
                325                 330                 335 ctc aag gag gcc tcc tga                                             1026
Leu Lys Glu Ala Ser
            340

<210> SEQ ID NO 5
<211> LENGTH: 180
<212> TYPE: DNA
<213> ORGANISM: Thermus sp.

<400> SEQUENCE: 5
ctataacggc cttttaggag ggggattgc cagccgctgg gctgacggtt attttggacc      60
cataaaaagg cgaaaccgag gcggttgccc cggatcaccc ccaagaccta gggtaacgcc    120
tcgggctcca gatgacaagg aggtccgagg gtgaagaacg aaaaaacctt ctttgaagag    180

<210> SEQ ID NO 6
<211> LENGTH: 5849
<212> TYPE: DNA
<213> ORGANISM: Thermus sp.

<400> SEQUENCE: 6
tctagaaggt cagggtggac aaggaaaaca ccatagcccc tgccaagaag atggacgagt     60
tggtgtccgg aaaagtggcc atccggggcg ctcttgacaa ctattttcca gcggtggcca   120
ccggcattgg ccacgaggta cgagcttgtg gagtagacgg ccacaaaggg gtcgtcctca   180
aacttctttt ctagtgccgc ttggacgaag gggaggaaga ggaaaggctt catggcctca   240
cctccttccc ctcctccttg gcggccttag cggcgtaaaa ctctgagacg gcctgaagtt   300
tagggatttc gctttcgggg ataagaatcc ggcggctcag gggatgccgg atggccctta   360
tcctgccgtc cctatgtac tcgtaaatgg tggccttggg tactttaaac cgttctgaaa    420
cttctctaac agagagcaca aaacctctaa aaacctatca atcccaccga ttccagtata    480
ccataaatgg cacaaagttt tgagaaggtg gtcaaacaaa aaggctttct cggtcaggtt    540
atggtgaggt gggggcggtc aaaggccgac ttaagtttgg taaagccggg aggaagcaaa    600
ccggggtgtt accatgcaac agatggccga gtggaacgtg tggacacaga gaagcgttga    660
gcttctggag aaggggtatt tggataaact actgcaggtc tataaagggg aaagtggctc    720
ttcgaggtca gtaccagagg aggtagagga aaaacttcgc gaggcctaca aggcatacga    780
ggggaggcag gatagtccgg aggcagaaac gaaactcgtg gaagccgtgc taaatgccag    840
aaaaaaggtc gagcggtccc ccttcaatca cccctacctg cctttggtct actacctggt    900 ttcgaaaaa gcagaaaaag cgaacaaggc ccttgaggag cattgcagg aggttgcctc     960 aaagcaccca gaaccatcc gcgtcctggc caaggaagcg caaagaagag gcgtagaagc    1020
cttgatccaa aggctcaagg agcctcccga aataaatcgg cagataggc cgatgttcaa    1080 aaggtggtac aaagaagagc taaggggaa atagaagag aggcttccag gccctaccaa     1140
accaaagatt gtggtagtat cccctgaaaa agtaaaccg gagcaagcac ccttattgc      1200 ggagagagaa gcgggcatca tcatatacac gggatcggat gaagctttga agatgccgc    1260 caaggaaaac ctgggccttg gcgaggaagc agaactaggc accaagggcg tagatttcta    1320
cgtggtcatc cggcgtagcc ctgaagagac atggcaccta acaggagaag tgaagtttca    1380
```

-continued

```
atccgacttt ggcggaaacc aagacaacca gaaactagta gcaaaggctt ccataaggtt    1440
ggaccttgag aagaggcaca taggaatagt ggtggtggac ggaatgcctg tggtgagcaa    1500
gtttcgtggg tgggccggac tggggaaaga acgatcgtt  acatccgtac tcctccttcc    1560
agacctgata gcggagctct accaaaaggg tgaagaagcc ctgggcctct agaaggcgga    1620
cacaatctca aacttgtgct gtagcctggg gaaatcctct aacacccttc tagtgaaggc    1680
tttgaccgcc tcccaggagg catctatgcc gatggatcgc cgctttaaga ggggtgaggc    1740
tataagcgta gtaccggagc ctgcgaaggg atcgagcact aaatcccct  cgttactccc    1800 tgtttggacg atgagcttga gcatgtccag atttttctcg gtggggtatc gcgggtacgg    1860
aggatccttg aactgccaaa cgtcctggag cttcttcccc ttcttcaggc gatcccgagc    1920
gtaaactttc ttccgcggca ccccgttctt tgaccagaca ataagccctt gagcgtctag    1980
ctcgtcaagc ttctccgggg gatagcgcca atgccgtcca ggaggggaa  gtattcctcg    2040 ccaaggcctt ccggtagggc catccttggt ttctccagga gcatgcaggg gattggtggt    2100
gtaccgttcc ccgttctcgt ctacaaaggg gaaaagccta gcgatctcct cttccgaata    2160
ggggctagcc gattcgttcc aaacgtagtc ccgcgttttg gagtagacga ggatcatgtc    2220
cttttgcgat ccgaaggcct tacgggaaaa gttttt ggga tttgaagcga tgcgggcgat    2280
atggttaacg aagtttcgcc ggccaaagac ctcatcaagg atgagcttca cctcgaaccc    2340
gtatttctcg tctatgtgaa cgaagatcag tcctgagtcc gccatcagct ccctgagaag    2400
tatcaagcgc tccctcagga actccacaaa ctgaggacca tcgagggtgt catcgtagcc    2460
caactgaccg ttttt gggct ggctgacggt agcaacgcga tctgtttcat cgccgccaac    2520
gagaaactgc tggccggttc cataaggcgg gtcaatatag accaactgga ccttccccgc    2580 atcccacca  ggctcccgga gcatccaccg gagaacctga ccgttttccc ccaaaaagta    2640
ggtgccaata ggatcaatct caaaaagggg ggcatttccc cctaggaaga ggagggtttc    2700
ttttcgcaaa acaagttgtg gggtgggctg atcaagaatc tccttctcat cgcgttttcc    2760
ggggtagacc aacctaaagg gcgaaggttc cgaggttttc gaggctttca agggggcttt    2820
tcgggtcaaa ccagggtagc tacggctcat tcttccctcc ccacagcgct cttaagcagg    2880
acctcatcac ccacaaccct cacgcactcc aaccaaggaa tccgccaaag gcggcctacc    2940
ttttgagccc gtatcttccc ctgacgtata gaccttcgga tcgtctcagg gtgcacccga    3000
aggatgtctg caagctcctc gggggtcagg tacgcgggct tcatcctcat gacacaacct    3060
taccccacag aggacaacac atgcaactat gggcaaagta gacaacgaga ccaaaagctt    3120
gggccactct ctcaggaggc ctccttgagg gtcttcacta ggtacgctcc cggtcgtgtc    3180
agatggccat ccgtgtaatc tcggataacc cgcattagga cggcaaatag atattgcgcg    3240
gggagttcac ccctggccac agcccacagc aagcctgcat agaaacgtct tgaacgacgg    3300
tcatctagga gatcggcaat gtacgtagca atgagggtga taagggccgg gagtttggaa    3360
cgctccacct cggggaggac caggatgagg cccaggtcaa cggccacggt cttggtgttg    3420
ggcatcaccc ttttcccctg agcccagagg accagcacgt ccagggtggg gcggattccg    3480
tggtcctggt aggccttgac ccagttgaag gagagcacgc cgttggccat gtctagggcg    3540
aggttcctcc aggggtagat gtagtcgtcc agggtgagcc tggctttccc tggcctcagc    3600
cggacggccc aaagggtgcc gatggcccgg cgctccccgt tgacggtttg gtgaaggacg    3660
tcggtggcca ccaggccctt tttctcaagg accttcttcc aggcgtggac ggtctgccgg    3720
```

-continued

```
gtgaccccca ggttgagggc aacatctcc agggggacca tgaagacgac cgtccccacc      3780
ttcctccaga gctcccggtt gccgtagggg atggtggagc gggcaatctc ctggaggagt      3840
tccagaagct tctgaggccc gtcctggacg gcttgacata cattcccaac gggggttca      3900 gctggtggta taggggggc cccaacagag gaaaggaaag cctcatggtc tttctcgggt      3960
aaagcaatcc taagtgcctc ttttttggtat gtaaagccct tcgcgaggcg attttcggca      4020
cctccatctg gagggggtc ggtggccaag aagaagtcct ctgaccccct atctgacccc      4080
ctagtggcat cggtgttgtc gtgggttttcc tctaaagcct cgtaaagctc ttcaaagaag      4140
gttttttcgt tcttcaccct cggacctcct tgtcatctgg agcccgaggc gttaccctag      4200
gtcttggggg tgatccgggg caaccgcctc ggtttcgcct ttttatgggt ccaaaataac      4260
cgtcagccca gcggctggca atccccctc ctaaaaggcc gttataggcc ctgctaggag      4320 ggggtagta ctttcctacc cccctaggct tggagaggcc ttaggaggtc tcctagggcc      4380
tcgtgggggt gtagggtaa cctcatggcc aggccggccg gctcgggact ctggaggagg      4440
cctccatagc ctactcgtgg tggaggtttg tgaagggtt cactaatgca tacggctagc      4500
ctcgggatca cggccaaatg gtatgcaggt tttggtataa aaccctcagg tttgaggcta      4560
gtttatgtcg gttttatgca cctttgactc ggatcacggg cataaacacc agtttcctgc      4620
acgaaagaaa actttcgcga tctaagaggg ggaaagaggt gtagagggac ggccttcatg      4680
aaagttggcc tcttaggagg ccgttgtaga gggccgtctc gggttcaaat cctttccctc      4740
tctctccagg tttccgaggt tcgaggtctt ggtccaggtc ttgtaccaag tttttgacca      4800
aagtctattc tcggaatata ggggtatctt gtctatcttc cctacgggat atctctgtct      4860
gtgtgaactt gatcccatcc caatacatat ctcaatctcc taatctcctc ttctctccag      4920
atccctaatc tcttcttcta cctctttctc ctcccaatta agaatggaga ggaaaaaccc      4980
cgaccagaac gagcttctcg gggtcagttt cggtaatctc gggacaggtt ttcatcgtct      5040
aggacgagga ttagggcatg aaaaatgggc tttgacaaaa tctttctaaa aaatactccc      5100
cgaggttggg gaagtgccct cggggagaag attttttggca gtttagatgt tatgctctat      5160
cacgggccgg aggcctccac gataagttgt cttggccaag taccgggcca ggtcgggggt      5220
gctcttcagc gtggtgatgg tactttcacg gaagttcaca agtcctttta gaggcttcag      5280 gtcgggata gtgctcaagt actcccaagc gttctcgggc ccgtggtcgg ggagaaggac      5340 aaagggtcg ggcaaaagtt catctttgta cttaggacgg attactttag cacctgataa      5400
cttcagggcc gttaagaagg gcctcacctc ggagacgggt ggaaggagga cgtgggcgtg      5460
gaagaagacg aaccccgatt tttgggaagt ctccctccag tttgatgatg aacgttggga      5520
ggaagccggc caggatgtct ttcatcgcgc ctcgaacctc ggacacataa aaaactttcg      5580
tgtttgtcag ggcaagagtg ctatgtatga ggtaaccttc gggagtacaa agtgcctcaa      5640
gccgcctttc ccaacgctcc aaaactctag ggtcaggtgg tttaggtttt ctgaaaaact      5700
ctagcttttc agtggtcatt cctcacccct ctagcacgta ctctggaagg taaacctttg      5760
acacagcggc caagtctagc gtctcccagt ccagttggtc tgggacgcgt gagaagggga      5820
ggggcttggt gtagaggacc agaagaccc                                       5849
```

<210> SEQ ID NO 7
<211> LENGTH: 603
<212> TYPE: DNA
<213> ORGANISM: Thermus sp.

<400> SEQUENCE: 7

```
atgatcgtgg ctgtcaccgg cttcaaggga ggggtgggga agaccaccac ggcggtccac      60
ctggcctgct tcctggccga gcggggcccc accctgctgg tggacgggga ccccaaccgc     120
tccgccacgg ggtggcaccg gaggggaggc ctcccggtga ccgtggtgga cgagcgggtg     180
gcggcccggt acgcccggga gcacgcccac gtggtcatag acacccaggc ccgccccacg     240
gaagaggacc tccgggccct cgccaagggg gtggacctgc tggtcctgcc cacgtccccc     300
gacgccctgg ccctggaggc cctcctggcc accctggaag ccctgcgggg ggcggaggcc     360
cgcttccggg tcctcctgac catggtgccc ccgccccga gccgggacgg ggaggaggcc      420
cgggccctct gggggcgga gggcgttccc ctcttcacag gctgggtgag gcgggcggca      480
gccttcccca aggccgccct cctggggggtg cctgtctacc gggtgcccga ccccagggcg    540
aggctggcct gggggggacta cgcgcgggtg ggggaagagc tcctgaagga ggtggggga    600
tga                                                                  603

<210> SEQ ID NO 8
<211> LENGTH: 11958
<212> TYPE: DNA
<213> ORGANISM: Thermus sp.

<400> SEQUENCE: 8
cttatacaca caaactatac acgtctctat cgggcttttc ttagcgccat gtaaaacacc      60
cctcccatct ccgggtgttt acagcggata cgggaggttc agcgggaact tttcccttg     120
ttgaaacttt ggggtctgag gctcaacagc agaacagctt aggttgactc aacacagctc    180
ataagtccct tcattatcgc ctgagtcaac ctatgagtta accttttttc aagaaaaaga    240
gataagtgag ttttgtcctc tagcacgact ttttctttg agtcaacctc tgtgccgacc     300
ccccgattt tgagtcaacc cccctttgag ccgaaacttt gttggcacag gggttgactc     360
aggggttgac tcaacgcgaa tggcctctgg aagggcgttg agccgacccc tccctcgtgt    420
gccgaccccc gctccactat gagcaggggg gaaagttacg ggaaaagttc cccaagtccc    480
ccttgacaaa agatgacaat cgagttaatg tcacagcgat gcgtcactca cctctggctg    540
ggctcaccca gatgcgtgcg cgaacgtttc agagcctcct tcgattcctg ccagggagg    600
ggcgctaccc cactggtgta gagctcgcca aggtgctggg gcgcagcccg cacgccacgt    660
gggccatgct cagggctttg acccgtcatg gactcgtgga acggcacgag ggggtctatg    720
ttctgacccc tgcgggcgta gaacttgcca ggacccttggg aaccaccgtg tggcgtgggg    780
atgaggaggt acagacggcg ttacagctgc taggagtcgg tcatgccgcc gaggacaggc    840
gctgaagctt tgagccggg gccctcaccc aaggccaccc cggctcctct cccctgggat    900
cccaaatgga tccctcagcg ccattatcct cctggcggtc ctatagcgca aggaggtagt    960
ggtgacgaaa cacacaaatg tttcacccca cctttggat gccgtagagg agctcgctcg    1020
ccagattgct gaaaccgcta acaaggctta ttccagccat ttcaggcaga ttgtcaaagt    1080
cctgccgcct gaggttcccg acctctacgc ctggctggcc gccctggatg actccgccat    1140
cgaggagctt gcccagcgcc tgagggaggt cgagggaagc cccgccccc atttcaccgc    1200
cgccctcaaa aaggccctgg ccatcgccct acagcggcgg accctcgccg agatgccccc    1260
cacgttcgcc aacgcgctcc gctgggcgat ggaacggcaa ggggtgagca tccgcaagct    1320
tgcgagagag gtaggggtca gcaaaaccac tgttaaaaag tggcgtggag gccgcttttgt   1380
ccctcgttca cggacctacg tgaggaggtt ggaggagatc ctggacctcc cggaaggcgc    1440
```

-continued

```
cctttcggga cgactacccc gctgggggtt gccaaaaata ttggaaggtg ttgaggggaa    1500
agatgcccct tatcccgggt tcacgcggac cttcctgcgc gtggccgccc tggcgcgcta    1560
cggccgcccg tgggatgatc tctctcccga cgaacaggag gcccttcggc gcgaggacga    1620
agaccggtgg acccgcctct ccaaccgcca gaagcgagtg cgaaaggcca gtcaaaaacc    1680
ttttcggctt tcctttgacg agtggccaac tgaggctcgc aaagaatggg aggactacga    1740
gcgctatgcc tcatcggcac ctgggagcat cgcgcgcgtg caggcggcgc ttgcgggcgc    1800
acctctcgct cccacgaccg tgcggacgga aacgctcgag cgtgagcgga tacttataga    1860
actgttctac ggctactgtg taaacgaacg gggcctcgca agcaacgcgt tgagcctcgc    1920
cctcctcaca gacctggagc tcgtccaatc gtacctggag tggcgcgtga ataggtacaa    1980
ggacgaggat ttacccccg ttactcgatc ggaatacatg tttatcgccc tggtgaaaaa    2040
actccacaga ggttatctcc gcgcccttgg gcttgggta  gacccggacg gggtgaaaga    2100
gctgaacgg aaactgaaaa tcgccggaat tgatgtcacg gacggctacc acgcggtgga    2160
gcccctcctg gaaactcacg agcccctccg ctgggtgctg gatggcatcc ggctcatgct    2220
ccgcgatgcg gcggggcggg taggcaacct gctgacaccc caaatcccca ccgccaaaag    2280
cgaagcgggc gaagcgttcg ccctctaccg ggacgtcgtt ctgctttgga tgatggtggg    2340
ccaccccctc cgggcgaagc attactacga agctcgcttg gacatgagcc agttccaaga    2400
cggggatttc gctcccgggc ggggacacgt ggggcgggcc ggcggagggt actacctggc    2460
ctaccgcaaa gtggagttca aaaacgcccg aggccaggtc tttcagagcc tccaggacca    2520
cgatctcgtc acgttccccc tggacgaccc cgagcaccct gtcctggtcc tggacgtgaa    2580
cgggatgcgg tactccctca cgagctctt  tcacgtctac ctgcgcacga tcctctcccg    2640
cctggcccag gcctgggccg gaccggtccc ctcctgcccc tgtttccggg tgccgatacg    2700
aggctcagac ttgcgcacat cgttcgcagg gcgcgccgcct acgtggccgc cgtgcccggg    2760
gtaccccaga aacttttgcc cttcggcccc cactccatcc gccacgtggt ggccacggag    2820
gtcgtgaagc gcacgggctc tttttgaggcc gccgccaacg tgctcctgga tagcatagac    2880
atggtcgttc gacattacgc ccgttcgttc cccgcgaccg taacagtcac ggttggcggg    2940
ctaacgcccg cgcccgggga ggtgagcggt gagggacctc cacgactttt tcctggcccg    3000
ggtggacgaa ctggtgccgg aactcctacc cggggcgcgg cgggtgggcg acgagtggcg    3060
ggcgggctcg gtccagggcg agcggggcga cagcctggcc gtggaccgcg gaagggctt    3120
ctggatcgac cacaacccct cggccccga  gccccggcag ggaaacctcc tcacgctgat    3180
ccaggcggcc aagggctct  cccccgagga ggcccggcgc tgggcccagc agtggcttgg    3240
cctctcccct tcgccaaagg tcaggcggac gaggagctca ggaccaaagg tcttgagtac    3300
tcaagtgcgt gggagctcgg gtgctccagt ccctgagtct tcaggttccc aggtacctga    3360
ggagtcggac ccctttgaca accccgctt  ccggacctc  ctcacccca  ggggcgagga    3420
cgaggccccc ttggccccgg cctccgagga ggtgctgcgg cgcatggtgt ctaggcttct    3480
ccgcacccc  gaggccgtgg cctacctgaa ggggcgcggt ctggatgccc gggtggtccg    3540
ccgcttctac ctcggcctgg acgacaccgc gcgggccacc gccgccctgg tctacccggt    3600
gataggccg  gacggctccc ccgttcgccg ccacctctac tacgagatcc ccggcctcac    3660
ccagggcgcc ccgggcaagg gctggggga  ggggaggccc accagctact gggccctccc    3720
cccctttcgag ggcccctccc ccgccgcaa  gctcttcttg tgcgaggggg cgaaggatgc    3780
ctgggccctc tggctccacc tccacgccca gccctgggcc caggacctgg cggtggtgac    3840
```

-continued

```
ctccacgcac ggctccgccc tccccgaggc ctggaaagac ccctgttct gggccccttg    3900
ggaggaggtc tacctgggcc aggacgccga ctccgccggc gaggagatgg cccggaaggt    3960
ggcggaggtg gcgaggcggc ccgtccgccg cgtccgggtc ccgaggggga tggggaagga    4020
ctggacggac tacttcctgg cggggggcac ccccgagggc ttgcgcctcc tcctggaggg    4080
agcggaggtc tgggaagaag aagtggctgg aggtggggcc aggatccagc tcccggaccc    4140
cgtggacatc cagcgggcct cgtgcgggg ccacctctac gtccccgtgc gggtcctgga    4200
gaaccggggg gaagaagggg cccgctaccg caccgtggtg gtccgctccg acggggccgt    4260
cctgggctgg ggctacttgc cggccccgcc cggcaccccc ttggaggacc gggtgctggc    4320
cgtggacgac ggcaccatca tccgcaggcc cccgaaggcg gccgccggga cctcgtggaa    4380
cggggaggcc atcaaccgct tcctggaagc ccgggcccgg ggagtgagcg ccatgaccgt    4440
ggccccccgg gacctgcctg ggctcatcgt ccgccacctc cgccaggtga tcctccccag    4500
tgaggacggc tacctcctgg ccgccttagg ggtcatgacc tcctacgtgc agagcgtctt    4560
cgacgccgtg ccctcttcc tcgtggtggg cccgccgggc tcggggaaga cggagttcgc    4620
ccgcctcatg gccgagctgg ggccaacgg cgtggtgatc accggccaga cctccgccgc    4680
caccgccgcc cggatcatcg acgagacggg ggggctggtg gccttcgacg acctggagga    4740
ggtgcgccag cggtcgggga cgctgaggc ctcccagctg gagcagttcc tcaaggtgtc    4800
ctacaagaag gagaccgcgg tcaagagctg gacggacacc aagggatgc gggtcctcac    4860
cctcaacttc ttcgggtca aggtgatcac caacacccag gggacgggg acatcctggg    4920
gagccggatg ctggtcatcc gcaccgcccg cctccgggac ctgggcagag gggaggagcg    4980
ccgccccgag gggctctccc ccccaggccc tccaagaact ccgggacaac ctctacatct    5040
gggccatgga gaacgcggcc agcctccacg ccctgtaccg ggagcgcttc gcgggcaagg    5100
gggagcgcct ggacgagatc gccgcccct tgcgtaccat cgcccaccac ctggggacg    5160
aggagctggc ggcccgcctg gaggacgccc tgcgccggca ggaagggcgc ctggaggaga    5220
cccttttccga tgccgaggtg gtggagaccc ccctcaagga ggccatccgc cagggctacc    5280
ggagccacgt ggccctggtc cacgtgatct tccaggcccg gaagatcttc ggggacgact    5340
ggggccggga gcgcaccgtg gacatccccc ggtggcggga ccccaagtgg gtggggcaga    5400
tcgccagcaa ctacggctgg gcggcccag aaaggcccgt gaggccccgg ctttgggaca    5460
agcagttccg catcatgcgc ctggagccca ccttcgtgga gcggtggtc aggggcttcc    5520
tccaggaggg gatcccctt gagcccctga agcaaccct ggcttctgcc tggacacccc    5580
ctgcgccgag tgcgcctacc tgcactggtg cgacctccgg cctgacaagg aaaagtggct    5640
ggagcgctac ggggaggcca agctggccca gaaaaggcgg gagctggagg aggagttttt    5700
ggccctggtg gggcccaag atggccttgg cctccaggct tccgccgagg aggagggaga    5760
ccgaggtaag cacccaagta cccaagtacc caagacccta aagcctcagg taccggagga    5820
cctcggggac ggaggaccta aaccccaag ggcgtgaaag actgaggtga gagggatgat    5880
cgtggctgtc accggcttca agggaggggt ggggaagacc accacggcgg tccacctggc    5940
ctgcttcctg gccgagcggg gccccacct gctggtggac ggggaccca accgctccgc    6000
cacggggtgg caccggaggg gaggcctccc ggtgaccgtg gtggacagc gggtggcggc    6060
ccggtacgcc cggagcacg cccacgtggt catagacacc caggcccgcc ccacggaaga    6120
ggacctccgg gccctcgcca agggggtgga cctgctggtc ctgcccacgt ccccgacgc    6180
```

```
cctggccctg gaggccctcc tggccaccct ggaagccctg cgggggcgg aggcccgctt    6240 ccgggtcctc ctgaccatgg tgcccccgcc ccgagccgg gacggggagg aggcccgggc    6300
cctcttgggg gcggagggcg ttcccctctt cacaggctgg gtgaggcggg cggcagcctt    6360
ccccaaggcc gccctcctgg gggtgcctgt ctaccgggtg cccgacccca gggcgaggct    6420
ggcctggggg gactacgcgc gggtggggga agagctcctg aaggaggtgg ggggatgagc    6480
aagttcgcca ggctcctcaa agaggtcaag gagaaggagg aggcctccgg ggagcggcct    6540
cgggggaaga gccggcggga ggactacgtg gccatgaagg tctacatcag caaagagctt    6600
caccggaggc tgaagctgaa ggccctggag gaggagaagg agctttcgga gctggtggaa    6660
gaggccctga ggaagttgct ggtgtgacct cctcccgcct cgtagagcgt gaaaaggagg    6720
taagacgatg gtcacccctta acaaatcgcc cctagaagcc ctctacgcgg gccactcccc    6780
ccaggaggcg ggccgtctct tcgaagcgcc tggtccgcaa gatattgaag gaactccacc    6840
ccatctggag ccaagagttc gtggatgtcg tcccttggtc cgagcacgcc acccgcaagg    6900
ggctcagggc cacggacatc ggcgtggacc tggtgggcta cgggaaggac gacaaggtct    6960
acgccatcca ggtcaagctg tgggataagc ccctctcttg gaaggacctg gggagcttcg    7020
tgggggtggt gaaccacccc gagtacggct tcgaccacgg gctcatcgtg gccccaagag    7080
gcgtgaccca ggaggccgac cgccagctcc agggcctacc catcaccatc ctgagcgaag    7140
aggctctcct agaagacctg gacctggaat ccctcgttcc agaccgcccc gaggaagccc    7200
gcaggcgggg gaagaaggcc ctccgtaagt accagcaaga agccttagag gaggtggcca    7260
aagccttctt agagaagggc ctgccccggg gcaagctcat catgccccg gcacgggca    7320 agaccctggt ggccctcaag atcgccgaaa aggtggcggg cccggggggg aggtcctct    7380 tcctggcgcc ctccatcgcc ctcctggacc agtccctcag ggcctgggcg gcggaggctt    7440
ccttgccctt cgcctcttc gccgtggtct cggacacggg cgtgggcaag acctcggagg    7500
acgacctctc cgccctctcc ctcctctcca tccctcctac caccaagcct gaggagctgg    7560
cctccgaggc caagacggag agtcaggagg ccctcaccgt ggtcttctcc acctaccagt    7620
cggcggaggt cctggagagg gcccagaagg agcacgggct tccccctttt gacctgatga    7680
tcctggacga agcccaccgc acagccacgg tgcgggcggg agaagaaagc cccttcacca    7740
aggtgcacca cgaccactac gtgaaggccc gccaccgcct ctacatgacg gccacgccca    7800
ggatctggga ggtggagggg aatggagaga ggggccaagg gaaaaaggcg gggaaaaaga    7860
aggaccctca gaaagagggt tctcctcccc ttttggacct cggtgcctct cctacggagg    7920
actccacggc ccccgaaggg gtggaactcc tggtctactc catggacaac gagggggatct    7980 atggccccac cctctacgag tacaccttca cccgcgccgt gaaggagggc cacctgagcg    8040
actacaaggt catcgtcttc tccgtggcgg aggaagccca aaaggacctg gcctcctacc    8100
tccagggacc cgaggccctc aaggtggagg aggctctgaa ggccctgggc ctgtggaagg    8160
tcctccaggg ggaggtgcgg gacgaggagg ggaacccgat gggggcctc gacctgcgga    8220 gagtcatcgc cttccacggc cgggtgaagg agtccaagga gatggaggaa gagttcacga    8280
aggtggccct cgctgcccag caggctggcc tccttcccga ggagctccgg cgggtggagg    8340
tgaagcacat agacgggcag atgtccgcct atgaccggaa cgcctcctg gactggctta    8400 gggagaacgt ccccgagggg gaggtccgcc tcctcaccaa cgccaaggtc ctcaccgagg    8460
ggatcgacgt cccggcccta gatgccgtgg ccttcatgcg tccccgggac agcgtggtgg    8520
acgtgatcca ggccgtgggg cgggccatgc gcaaggcccc gggcaaggag tacgggtacg    8580
```

-continued

```
tggtcctgcc cgtggtggtg aggggggcagg acgaggagcg ggagatcgag gagagcggct    8640
accgggcggt gtggcaggtg ctctcggcct tgcgctcggt ggacaagtcc ttcgaggccc    8700
gcatgcgggc cgccctggtg cgcctctcgg gtaaggggcga gggcgggggaa ggtggagagg    8760
cccgagaggg tgtggccgtc atcggggaag gaagcgcctc ccccgtgatc gtagatgtcc    8820
ttcaggggaa cctcaacctc caccaggaga tcacccggag cctcgccggc aagctggtca    8880
ggcgcctcgc cctggggcgg aagtacctgg agaactgggc ccaggacgtg gcccgggtgg    8940
cgaaggtgct ggagcagcag gtcagggcga tggcggagcg ggaccccaag gtgaaggaaa    9000
aactggggaa actcctcgcc gccctgcagg ccttcaccag cgagagcgtg acggaggacg    9060
aagccatcct catgctggtc cagcacgctc tcaccaagcc catcttcgac gccctcttcg    9120
ggaactcct agaaaagcgg gaggaccccg tttcccgggc cctagacgaa ctcttccagg    9180
agttcagggg gttcctggac cgggaagggg aggccctcaa ggatttctac gaagagatgc    9240
gcctcaaggc cctagggctc acggacgaag ccgaaagggc cgacttccta cggaggctct    9300
actccaactt cttcgcccgg gccttccccc aggtggccga ccaggtgggg atcgcctaca    9360
ccccggtgga gctggtggac ttcctggtga agagcgcaga cgagctggcc aggaagcact    9420
gttggccggg ggctcgatgg ggagaaggtc ttcatcctgg agcccttcgc cggcacaggc    9480
accttcgtca cccgaatcct gcaccgggta gccgaaaggg gcggggccga cgcggtcaag    9540
ggcaagctgg agcgggggga gatctgggcc aacgagatcc ttctcctccc ctactacgtc    9600
ctcagggcca acgtggagaa caccaccctg gccctgaccg ggagtacgt cccttcaag    9660
ggggcgttct ggcggactcc ttcggctggc ggagctgggg tatagcgaga aaaagtttgg    9720
catcatcccg ctcttcccgg aagaatacg tgaggccctg aacgagcagc tgaaggcccc    9780
tatccaggtt atcctctcca acccccccgtg cgggcttggt tggagaagga gggcgagggg    9840
aagaagaacc ccgtctaccg taaggtgcgg gagcgggtgg agccaaccta tgtacgcgg    9900
gccaaggaac ttcccatcgg ggggacaaaa cccaagggag agaacctgaa ctccctctac    9960
gaccagtaca tccaggcctt gcgggtggcg agcgaccgta tcggggagga gggggtcgtg    10020
gccttcgtca ccaacaacgg gtggctgggg ggcgtagtgc cccggggctt gcgggcctct    10080
ttggcggagg agttcgccga ggtgtacgtc tacgacctga ggggggatgc gagggagaag    10140
ggggaggcac ggaagaagga gggggcggg gtctttggac agccttcccg cgccggggtc    10200
tgcctcctcc tcctggtgaa gcgtaaggac cacaaaggga tcggcaaggt ccacctctat    10260
cgggtcgggg acggcctctc ccgggaggcc aagctggctc tggtgaagga gcatggctca    10320
gtctctgggt tccctggcaa gaggttccct atgaagagtg ggtggggagg cttaccccccg    10380
ggttctcggg gatgttgtcc ctggacgagg tctttgaggt gcggagttct ggggtgaaga    10440
ccaaccgcga tgcctacgtc ttcaacccct ccgggcgga gctggagcgg acatgaggc    10500
ggctcatctc cacctacaac gagcacgtga aaggaaaaa agagggggaaa ctaggggaac    10560
tggaaaagga tgagagcatc atcaagtggg atagggaact catcaggtac ctagagtccc    10620
tgagggaagc ttcctacgaa gggagcggtc aagtctacga ggccctctac cgccccttcg    10680
tgcctatgta cctctacctc agccgcactt tcaatagcat gatttaccaa atccccgca    10740
tctggcccac ccccgagggcc gagaacctgg ccatcgccgt ggccggaaag gggagtaacg    10800
cttttagcgc tgtggccacc aggagggtgg ttgacctgca ctttattgag accacccagc    10860
tctacccccct ttaccactac cccgaaaaca gccctctggg gggacaccca aagcgcaagc    10920
```

-continued

```
tcaacctcaa ggaggagttc ttgaggaagc ttgggaggt cctcggccgc ccgttcccc      10980
ccgaggaggc cttcgcttac atctacgccg tggtgagcca ccccctctac gccgagcgct      11040
tcgccaagga cctcaagatg gacctccccc gcattcccct cccccaagat cccgaactct      11100
ttgccaggct ggtgaaggcg ggtcaagaac tcattcacct ccacaccgag tacgagaccc      11160
tgccccctg gagcccagtc ccccttcggg tggaagaggg aggcccggag accctacga      11220
gcgctaccgg gtggagcgga tgaggctgga caaggagagg agggttctcc agtacaacga      11280
ctgggtccgg gtggagggca tccccgagga ggccttccgc tggcgccccg ggggtactc      11340
cccttggag tggattggcc gcttctggaa ggtggaggag aaggtgccca agggcagggg      11400
ggaggccatc gtctgggacc ccaacctctt cctcaaggag aagggggaac cccgttacct      11460
cctggacctc atcgggcggg cggtccaggt ggccgtgcag acggttggga tccacgagga      11520
gctgagagaa gacgtggaag ctctgctggg ttgaggggt gctggcccgc cgttctccct      11580
actcctttag ggcctacccc tacgatccaa gcacggccct gggggcgct caggtgggca      11640
tcccacgtcc aaggccccga cttgggcacc ccatgctgcg aacttacagc ccaagggcct      11700
gaaacattcc ccctgctca cggggggaaag ttcgtgaagg aaagagcaaa gccttttta      11760
tcgcatccgg agagatggcg gggtggaact tttccccgag gactccccca tagggacatg      11820
taaacggcaa gctatcagtg tagactttt tcaaaagag ccatactcgt gttttcccgt      11880
tcagaacggc atttttgcta aggaggtggt ttacaaatgg gtgttaatgc gctacatcct      11940
ccggtagtag gagcatgc                                                   11958
```

<210> SEQ ID NO 9
<211> LENGTH: 10
<212> TYPE: DNA
<213> ORGANISM: Thermus sp.

<400> SEQUENCE: 9
ggcttttctt                                                                      10

<210> SEQ ID NO 10
<211> LENGTH: 10
<212> TYPE: DNA
<213> ORGANISM: Thermus sp.

<400> SEQUENCE: 10
aacttttccc                                                                      10

<210> SEQ ID NO 11
<211> LENGTH: 10
<212> TYPE: DNA
<213> ORGANISM: Thermus sp.

<400> SEQUENCE: 11
gacttttttc                                                                      10

<210> SEQ ID NO 12
<211> LENGTH: 7
<212> TYPE: DNA
<213> ORGANISM: Thermus sp.

<400> SEQUENCE: 12 aactttg                                                                          7

<210> SEQ ID NO 13
<211> LENGTH: 7

```
<212> TYPE: DNA
<213> ORGANISM: Thermus sp.

<400> SEQUENCE: 13 agttttg                                                                 7

<210> SEQ ID NO 14
<211> LENGTH: 7
<212> TYPE: DNA
<213> ORGANISM: Thermus sp.

<400> SEQUENCE: 14 gattttg                                                                 7

<210> SEQ ID NO 15
<211> LENGTH: 7
<212> TYPE: DNA
<213> ORGANISM: Thermus sp.

<400> SEQUENCE: 15 aactttg                                                                 7

<210> SEQ ID NO 16
<211> LENGTH: 25
<212> TYPE: DNA
<213> ORGANISM: Thermus sp.

<400> SEQUENCE: 16
ggttccataa ggcgggtcaa tatag                                            25

<210> SEQ ID NO 17
<211> LENGTH: 25
<212> TYPE: DNA
<213> ORGANISM: Thermus sp.

<400> SEQUENCE: 17
ctatattgac ccgccttatg gaacc                                            25

<210> SEQ ID NO 18
<211> LENGTH: 27
<212> TYPE: DNA
<213> ORGANISM: Thermus sp.

<400> SEQUENCE: 18
gtggggtggg ctgatcaaga atctcct                                          27

<210> SEQ ID NO 19
<211> LENGTH: 27
<212> TYPE: DNA
<213> ORGANISM: Thermus sp.

<400> SEQUENCE: 19
aggagattct tgatcagccc accccac                                          27

<210> SEQ ID NO 20
<211> LENGTH: 26
<212> TYPE: DNA
<213> ORGANISM: Thermus sp.

<400> SEQUENCE: 20
tcacccacaa ccctcacgca ctccaa                                           26

<210> SEQ ID NO 21
```

```
<211> LENGTH: 26
<212> TYPE: DNA
<213> ORGANISM: Thermus sp.

<400> SEQUENCE: 21
ttggagtgcg tgagggttgt gggtga                                          26

<210> SEQ ID NO 22
<211> LENGTH: 26
<212> TYPE: DNA
<213> ORGANISM: Thermus sp.

<400> SEQUENCE: 22
agatgtagtc gtccagggtg agcctg                                          26

<210> SEQ ID NO 23
<211> LENGTH: 26
<212> TYPE: DNA
<213> ORGANISM: Thermus sp.

<400> SEQUENCE: 23
caggctcacc ctggacgact acatct                                          26

<210> SEQ ID NO 24
<211> LENGTH: 25
<212> TYPE: DNA
<213> ORGANISM: Thermus sp.

<400> SEQUENCE: 24
ttggtatgta aagcccttcg cgagg                                           25

<210> SEQ ID NO 25
<211> LENGTH: 25
<212> TYPE: DNA
<213> ORGANISM: Thermus sp.

<400> SEQUENCE: 25
cctcgcgaag ggctttacat accaa                                           25

<210> SEQ ID NO 26
<211> LENGTH: 25
<212> TYPE: DNA
<213> ORGANISM: Thermus sp.

<400> SEQUENCE: 26
tagtggcatc ggtgttgtcg tgggt                                           25

<210> SEQ ID NO 27
<211> LENGTH: 25
<212> TYPE: DNA
<213> ORGANISM: Thermus sp.

<400> SEQUENCE: 27
acccacgaca acaccgatgc cacta                                           25

<210> SEQ ID NO 28
<211> LENGTH: 14
<212> TYPE: DNA
<213> ORGANISM: Thermus sp.

<400> SEQUENCE: 28
ctagtctaga ctag                                                       14
```

-continued

```
<210> SEQ ID NO 29
<211> LENGTH: 9
<212> TYPE: DNA
<213> ORGANISM: Thermus sp.

<400> SEQUENCE: 29 ttatcaccc                                                                9

<210> SEQ ID NO 30
<211> LENGTH: 9
<212> TYPE: DNA
<213> ORGANISM: Thermus sp.

<400> SEQUENCE: 30 ttatccgag                                                                9
```